United States Patent
Horstmeyer et al.

(10) Patent No.: US 11,490,817 B2
(45) Date of Patent: Nov. 8, 2022

(54) INTERFEROMETRIC FREQUENCY-SWEPT SOURCE AND DETECTOR IN A PHOTONIC INTEGRATED CIRCUIT

(71) Applicant: HI LLC, Los Angeles, CA (US)

(72) Inventors: Roarke Horstmeyer, Durham, NC (US); Haojiang Zhou, Los Angeles, CA (US); Haowen Ruan, Los Angeles, CA (US); Yuecheng Shen, Guangzhou University City (CN); Jamu Alford, Simi Valley, CA (US)

(73) Assignee: HI LLC, Los Angeles, CA (US)

( * ) Notice: Subject to any disclaimer, the term of this patent is extended or adjusted under 35 U.S.C. 154(b) by 848 days.

(21) Appl. No.: 16/392,963

(22) Filed: Apr. 24, 2019

(65) Prior Publication Data

US 2019/0336006 A1    Nov. 7, 2019

Related U.S. Application Data

(60) Provisional application No. 62/666,940, filed on May 4, 2018, provisional application No. 62/692,124, filed on Jun. 29, 2018.

(51) Int. Cl.
*A61B 5/00* (2006.01)
*G01B 11/02* (2006.01)
*G01B 11/22* (2006.01)

(52) U.S. Cl.
CPC .......... *A61B 5/0082* (2013.01); *A61B 5/0059* (2013.01); *A61B 5/4064* (2013.01); *G01B 11/02* (2013.01); *G01B 11/22* (2013.01)

(58) Field of Classification Search
None
See application file for complete search history.

(56) References Cited

U.S. PATENT DOCUMENTS

| 7,519,246 B2 | 4/2009 | Welch et al. |
| 8,654,320 B2 | 2/2014 | Hasegawa et al. |

(Continued)

FOREIGN PATENT DOCUMENTS

| JP | 2007114160 | 5/2007 |
| WO | 2015109005 | 7/2015 |

OTHER PUBLICATIONS

Houser et al., "Balanced detection technique to measure small changed in transmission", Applied Optics, vol. 33, No. 6, Feb. 20, 1994, pp. 1059-1062. (Year: 1994).*

(Continued)

*Primary Examiner* — Katherine L Fernandez
(74) *Attorney, Agent, or Firm* — Michael J. Bolan; Vista IP Law Group, LLP

(57) ABSTRACT

A non-invasive optical measurement system comprises a two-dimensional array of photonic integrated circuits (PICs) mechanically coupled to each other. Each PIC is configured for emitting sample light into an anatomical structure, such that the sample light is scattered by the anatomical structure, resulting in physiological-encoded signal light that exits the anatomical structure. Each PIC is further configured for detecting the signal light. The non-invasive optical measurement system further comprises processing circuitry configured for analyzing the detected signal light from each of the PICs, and based on this analysis, determining an occurrence and a three-dimensional spatial location of the physiological event in the anatomical structure.

44 Claims, 11 Drawing Sheets

(56) References Cited

U.S. PATENT DOCUMENTS

| | | | |
|---|---|---|---|
| 9,946,344 B2 | 4/2018 | Ayaz et al. | |
| 10,371,614 B2 | 8/2019 | Hosoda et al. | |
| 10,969,571 B2* | 4/2021 | Swanson | G01B 9/02004 |
| 2005/0049470 A1* | 3/2005 | Terry | A61B 5/14552 |
| | | | 600/323 |
| 2006/0093369 A1* | 5/2006 | Nagarajan | H04J 14/02 |
| | | | 398/135 |
| 2014/0376001 A1* | 12/2014 | Swanson | G01N 21/17 |
| | | | 356/479 |
| 2016/0238793 A1* | 8/2016 | Frankel | G02B 6/126 |
| 2016/0345880 A1 | 12/2016 | Nakaji et al. | |
| 2017/0227445 A1 | 8/2017 | Nakaji | |
| 2018/0249911 A1 | 9/2018 | Hosoda et al. | |

OTHER PUBLICATIONS

Dominik Wyser, et al., "Wearable and modular functional near-infrared spectroscopy instrument with multidistance measurements at four wavelengths", NEUROPHOTONICS, vol. 4, No. 04, Aug. 18, 2017, p. 1, XP055618655.

Hubin Zhao, et al., "Review of recent progress toward a fiberless, whole-scalp diffuse optical tomography system", NEUROPHOTONICS, vol. 5, No. 01, Sep. 26, 2017, p. 1, XP055619174.

Yanlu Li et al: "On-chip laser Doppler vibrometer for arterial pulse wave velocity measurement", Biomedical Optics Express, vol. 4, No. 7, Jun. 27, 2013 (Jun. 27, 2013), p. 1229, XP055619911.

Soren Aasmul et al: "Towards a compact multi-laser-beam device for cardiovascular screening", Retrieved from the Internet; Apr. 1, 2017 (Apr. 1, 2017 ), XP055619237; XP055619908.

Lefteris Gounaridis et al: "Design of grating couplers and MMI couplers on the TriPleX platform enabling ultra-compact photonic-based biosensors", Sensors and Actuators B: Chemical, vol. 209, Mar. 1, 2015 (Mar. 1, 2015), pp. 1057-1063, XP055619192.

Zhao Wang et al: "Silicon photonic integrated circuit swept-source optical coherence tomography receiver with dual polarization, dual balanced, in-phase and quadrature detection", Biomedical Optics Express, vol. 6, No. 7, Jun. 17, 2015 (Jun. 17, 2015), p. 2562, XP055620031.

C. Weimann et al: "Silicon photonic integrated circuit for fast and precise dual-comb distance metrology", Optics Express, vol. 25, No. 24, Nov. 16, 2017 (N0v. 16, 2017), p. 30091, XP055619005.

Artundo Inigo: "Photonic Integration : New Applications Are Visible", Mar. 1, 2017 (Mar. 1, 2017), XP055619204.

Wim Bogaerts: "Introduction to Silicon Photonics Circuit Design", Mar. 11, 2018 (Mar. 11, 2018 ), XP055617994.

Joost Brouckaert et al: "Integration of Photodetectors on Silicon Photonic Integrated Circuits (PICs) for Spectroscopic Applications", Oct. 25, 2010 (Oct. 25, 2010), XP055617942.

Marc Korczykowski, "Perfusion functional MRI reveals cerebral blood flow pattern under psychological stress", Departments of Radiology, Neurology, Psychiatry, and Psychology and Center for Functional Neuroimaging , University of Pennsylvania, Philadelphia, PA 19104; pp. 17804-17809, PNAS, Dec. 6, 2005, vol. 102, No. 49.

D. Borycki et al., "Interferometric Near-Infrared Spectroscopy (iNIRS) for determination of optical and dynamical properties of turbid media," Opt. Express 24 (2016).

M. A. Choma et al., "Sensitivity advantage of swept source and Fourier domain optical coherence tomography," Opt. Express 11 (2003).

Z. Cheng et al., "On-chip photonic synapse," Sci. Advances 3, e1700160 (2017).

Z. Wang et al., "Silicon photonic integrated circuit swept-source optical coherence tomography receiver with dual polarization, dual balanced, in-phase and quadrature detection," Biomed. Opt. Express 6 (2015).

D. Vermeulen, S. Selvaraja, P. Verheyen, G. Lepage, W. Bogaerts, P. Absil, D. Van Thourhout, and G. Roelkens, "High-efficiency fiber-to-chip grating couplers realized using an advanced CMOS-compatible silicon on-insulator platform," Opt. Express 18(17), 18278-18283 (2010).

C. Li et al, "Compact polarization beam splitter for silicon photonic integrated circuits with a 340-nm-thick silicon core layer". Opt. Letters (2017).

L. Chen, C. R. Doerr, L. Buhl, Y. Baeyens, and R. A. Aroca, "Monolithically integrated 40-wavelength demultiplexer and photodetector array on silicon," IEEE Photon. Technol. Lett. 23(13), 869-871 (2011).

C. T. Santis et al., "High coherence semiconductor lasers based on integral high-Q resonators in hybrid Si/III-V platforms," PNAS 111 (2014).

Gratton G., Fabiani M., "Fast-optical Imaging of Human Brain Function," Frontiers in Human Neuroscience, vol. 4, Article 52, pp. 1-9, Jun. 2010.

Eggegracht A. T., et al., "Mapping Distributed Brain Function and Networks with Diffuse Optical Tomography," Nature Photonics 8 (2014)).

Hill D.K. and Keynes, R.D, "Opacity Changes in Stimulated Nerve," J. Physiol., vol. 108, pp. 278-281 (1949).

Foust A.J. and Rector D.M., "Optically Teasing Apart Neural Swelling and Depolarization," Neuroscience, vol. 145, pp. 887-899 (2007)).

Scott A. Diddams, et al., "Molecular fingerprinting with the resolved modes of a femtosecond laser frequency comb", Nature Letters, vol. 445 Feb. 8, 2007.

Shijun Xiao and Andrew M. Weiner, "2-D wavelength demultiplexer with potential for ≥ 1000 channels in the C-band", Optics Express, Jun. 28, 2004, vol. 12, No. 13.

M. Shirasaki, "Large angular dispersion by a virtually imaged phased array and its application to a wavelength demultiplexer", Optics Letters, vol. 21, No. 5, Mar. 1, 1996.

Kevin K. Tsia, "Simultaneous mechanical-scan-free confocal microscopy and laser microsurgery", Optics Letters, Jul. 15, 2009, vol. 34, No. 14.

S.R. Chinn and E.A. Swanson, "Optical coherence tomography using a frequency-tunable optical source", Optics Letters, Mar. 1, 1997, vol. 22, No. 5.

T. Bonin, G. Franke, M. Hagen-Eggert, P. Koch, and G. Hullmann, "In vivo Fourier-domain full-field OCT of the human retina with 15 million A-lines/s," Optics Letters, Oct. 15, 2010, vol. 35, No. 20.

J. Fujimoto and E. Swanson, "The Development, Commercialization, and Impact of Optical Coherence Tomography.," Invest. Ophthalmol. Vis. Sci. 57, Oct. 1-Oct. 13, 2016.

The Scientist and Engineer's Guide to Digital Signal Processing, "Chapter 9, Applications of the DFT", 16 pp.

Shoji Kishi, "Impact of swept cource optical coherence tomography on opthalmology", Department of Opthalmology, Gunma University Graduate School of Medicine, Maebashi, Japan, Sep. 29, 2015.

Wen Bao, et al., "Orthogonal dispersive spectral-domain optical coherence tomography", Optics Express, Apr. 21, 2014, vol. 22, No. 8.

PCT International Search Report and Written Opinion for International Appln. No. PCT/US2019/028881, Applicant HI LLC, forms PCT/ISA/210, 220 and 237 dated Sep. 18, 2019 (23 pages).

Wenjun Zhou, et al., "Highly parallel, interferometric diffusing wave spectroscopy for monitoring cerebral blood flow dynamics", Optica, May 2018, vol. 5, No. 5 (10 pages).

Dawid Borycki, et al. "Reflectance-mode interferometric near-infrared spectroscopy quantifies brain absorption, scattering, and blood flow index in vivo", Opt. Lett. Feb. 1, 2017; 42(3): 591-594 (18 pages).

* cited by examiner

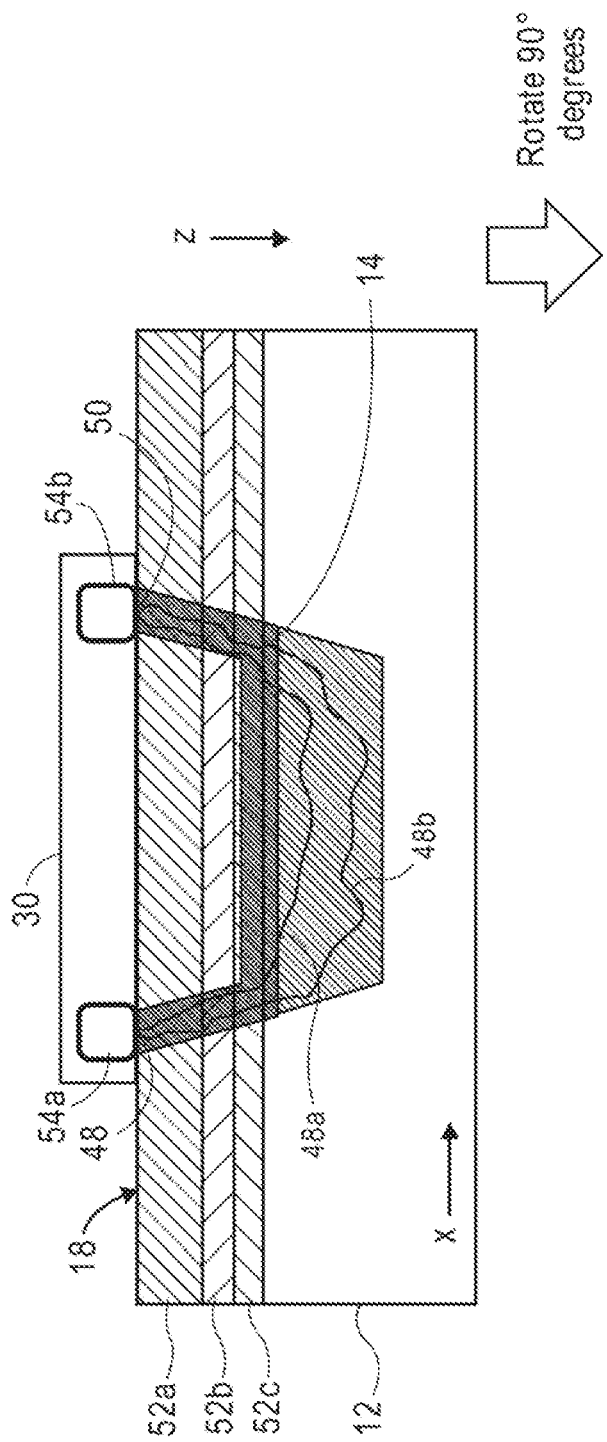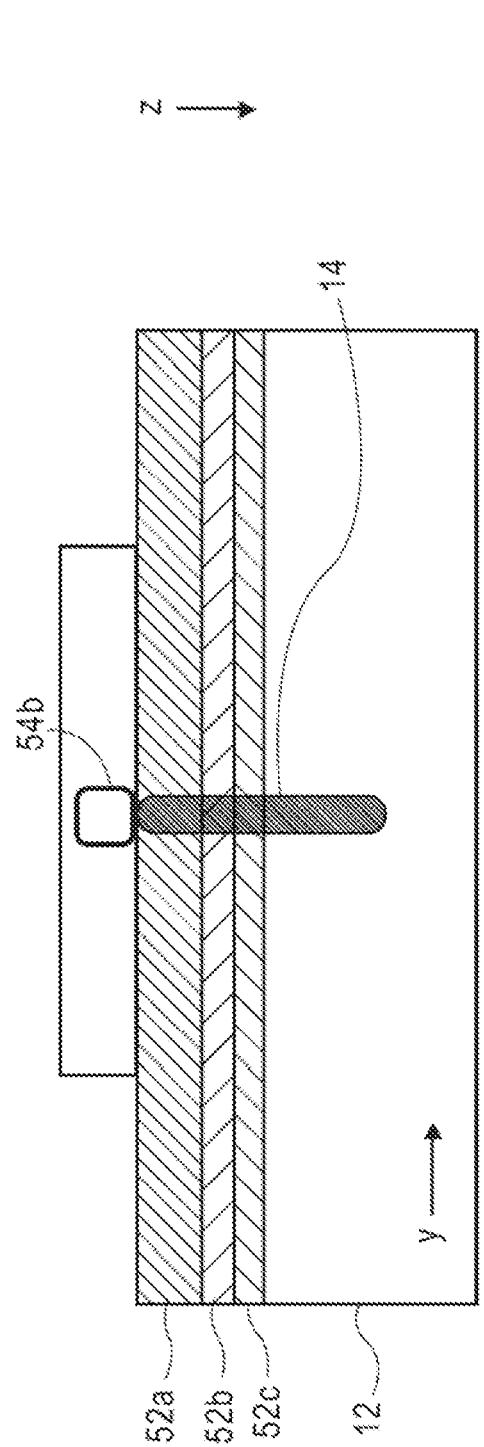

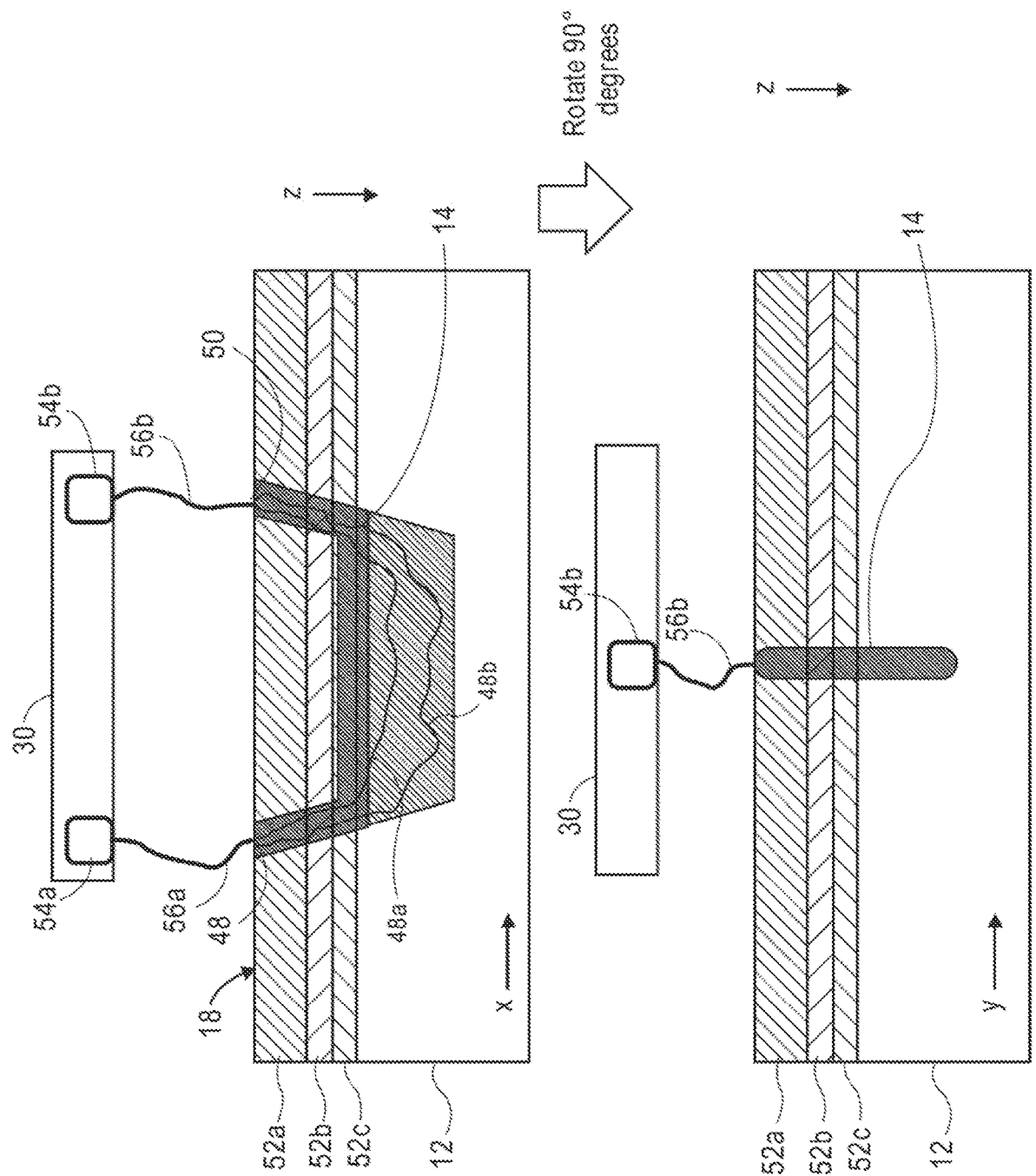

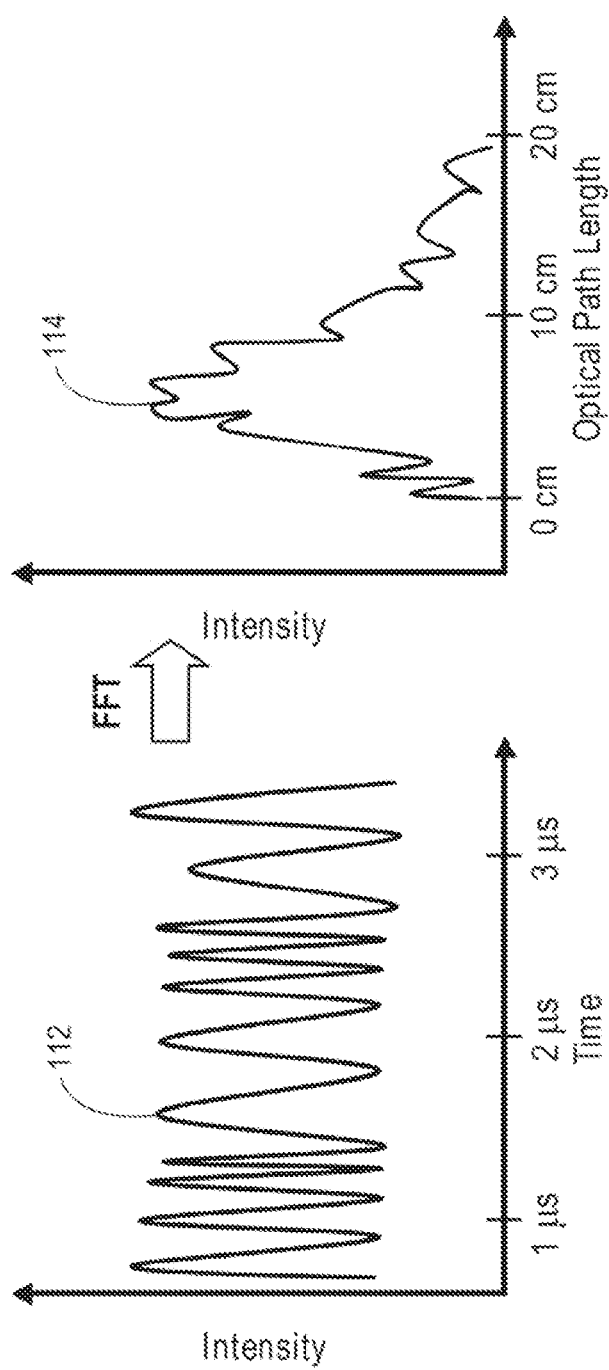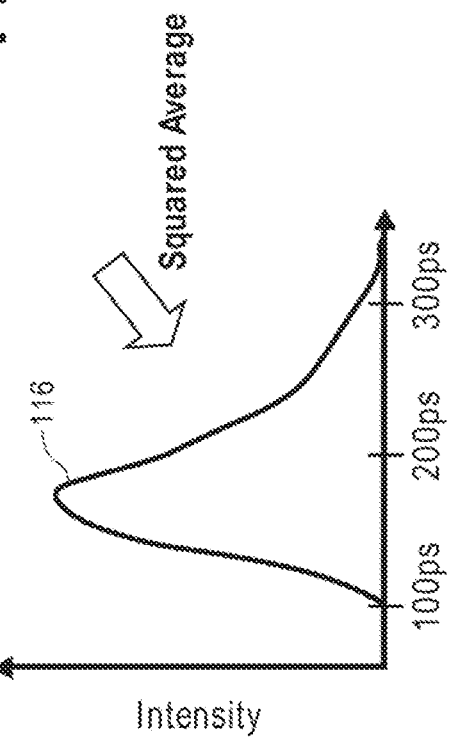

INTERFEROMETRIC FREQUENCY-SWEPT SOURCE AND DETECTOR IN A PHOTONIC INTEGRATED CIRCUIT

RELATED APPLICATION DATA

Pursuant to 35 U.S.C. § 119(e), this application claims the benefit of U.S. Provisional Patent Application Ser. No. 62/666,940, filed May 4, 2018, and U.S. Provisional Patent Application Ser. No. 62/692,124, filed Jun. 29, 2018, which are expressly incorporated herein by reference.

FIELD OF THE INVENTION

The present inventions relate to methods and systems for non-invasive measurements in the human body, and in particular, methods and systems related to detecting physiologically-dependent optical parameters in the human body, .e.g., the brain.

BACKGROUND OF THE INVENTION

Measuring neural activity in the brain is useful for medical diagnostics, neuromodulation therapies, neuroengineering, or brain-computer interfacing. Conventional methods for measuring neural activity in the brain include diffusive optical imaging techniques, which employ moderate amounts of near-infrared or visible light radiation, thus being comparatively safe and gentle for a biological subject in comparison to X-Ray Computed Tomography (CT) scans, positron emission tomography (PET), or other methods that use higher-energy and potentially harmful ionizing radiation. Moreover, in contrast to other known methods, such as functional magnetic resonance imaging (fMRI), these optically-based imaging methods do not require large magnets or magnetic shielding, and thus, can be scaled to wearable or portable form factors, which is especially important in applications, such as brain-computer interfacing.

However, because optical imaging techniques rely on light, which scatters many times inside brain, skull, dura, pia, and skin tissues, the light paths occurring in these techniques comprise random or "diffusive" walks, and therefore, only limited spatial resolution can be obtained by a conventional optical detector, often on the order of centimeters, with usable penetration depths being limited to a few millimeters. The reason for this limited spatial resolution is that the paths of photons striking the detector in such schemes are highly variable and difficult, and even impossible, to predict without detailed microscopic knowledge of the scattering characteristics of the brain volume of interest, which is typically unavailable in practice (i.e., in the setting of non-invasive measurements through skull for detecting neural activity in the brain for brain-computer interfacing). In summary, light scattering has presented challenges for optical detection techniques in achieving high spatial resolution deep inside tissue. Moreover, the diffusive nature of light propagation also creates challenges for measurements of fast changes in optical scattering inside tissue, since essentially all paths between source and detector are highly scattered to begin with.

Notwithstanding the foregoing challenges, the x-y (i.e., the plane of the surface of the skull) spatial resolution of diffusive optical imaging techniques has been increased by locating a multitude of optical sources and detectors along the surface of the head that, which despite the random propagation of light from the optical sources, can identify bundles through which photons are likely to travel during the random motion (see Gratton G., Fabiani M., "Fast-optical Imaging of Human Brain Function," Frontiers in Human Neuroscience, Vol. 4, Article 52, pp. 1-9 (June 2010) and Eggegracht A. T., et al., "Mapping Distributed Brain Function and Networks with Diffuse Optical Tomography," Nature Photonics 8 (2014)).

One commercially available non-invasive imaging method, referred to as optical coherence tomography (OCT), is capable of acquiring images with high z-resolution (depth), but at a relatively shallow depth (1 mm-2 mm). Traditional OCT systems u coherent light (typically light in the near-infrared spectrum) to capture sub-surface images within optical scattering media (such as biological tissue) at a micrometer-resolution. The OCT system directs an optical beam at biological tissue and collects a small portion of the light that reflects from sub-surface features of the biological tissue. Although most of the light directed at the biological tissue is not reflected, but rather, diffusively scatters and contributes to background that may obscure the image, OCT utilizes a holographic (or interferometric) technique to select, via optical path selection, the photons that directly reflect off of the sub-surface features (i.e., the ballistic backscattered photons), and reject photons that scatter multiple times in the biological tissue before detection.

In particular, in a traditional OCT system, light from a light source is split into two paths along two different arms of an interferometer: a reference arm and a sample arm. In the sample arm, sample light is backscattered through a sample medium, and in the reference arm, reference light is back-reflected by a mirror where it recombines with the backscattered sample light at a coupler. An interference light pattern is formed by any sample light that has an optical path length that matches, within the coherence length of the optical source, the optical path length traveled by the reference light. The intensity of the backscattering sample light having that optical path length can then be detected within the interference light pattern.

Previous commercial OCT systems acquire data in the time domain (TD-OCT), and coherence gates the backscattered light from various depths in the biological tissue by adjusting the position of the mirror to tune the optical path length of the reference, such that only sample light having the matching optical path length is selected for detection at any given time. An alternative approach to coherence gating, referred to as spectral domain OCT (SD-OCT) does not involve adjusting the delay of the reference arm, but rather involves acquiring an interferometric signal as a function of optical wavelength by combining the sample light and the reference light from a source with a finite spectral width at a fixed reference arm delay, and then Fourier-transforming the spectral or frequency-resolved interference as a function of photon time-of-flight to obtain the various depths in the biological tissue. Two distinct methods have been developed that employ the SD approach: 1) Fourier-domain (FD-OCT), which uses a broadband light source to achieve spectral discrimination; and (2) swept-source (SS-OCT), which time-encodes optical wavelengths by rapidly tuning a narrowband source through a broad optical bandwidth. It has been shown that SD-OCT has a significantly greater signal-to-noise (SNR) than TD-OCT (see Michael A. Choma, et al., "*Sensitivity Advantage of Swept Source and Fourier Domain Optical Coherence Tomography*," Optics Express, Vol. 11, No. 18, 8 Sep. 2003).

Regardless of the type, the depth at which an OCT system images biological tissue is limited, because at greater depths the proportion of light that escapes without scattering (i.e., the ballistic light) is too small to be detected. Thus, the clinical applications of OCT have, thus far, been limited to imaging sub-surface features, such as obtaining high-resolution ophthalmic images of the retina. As such, OCT is presently insufficient for measuring neural activity in the deeper regions of the brain (i.e., deeper than 2 mm).

Another type of diffusive optical imaging technique, referred to as interferometric Near-Infrared Spectroscopy (iNIRS) (see Borycki, Dawid, et al., "*Interferometric Near-Infrared Spectroscopy(iNIRS) for Determination of Optical and Dynamical Properties of Turbid Media*," Optics Express, Vol. 24, No. 1, Jan. 11, 2016), has been developed. While traditional OCT utilizes low-coherence interferometry to produce cross-sectional images of biological specimens with a resolution of few micrometers and an imaging range of 1-2 mm, the goal of iNIRS is to use high coherence interferometry to measure optical and dynamical properties of turbid media using high coherence interferometry at a depth on the order of a few centimeters, at the cost of reduced resolution.

Furthermore, the systems described above have not been demonstrated to measure fast-optical signals, which refers to changes in optical scattering that occur when light propagating through active neural tissue (e.g., active brain tissue) is perturbed through a variety of mechanisms, including, but not limited to, cell swelling, cell volume change, changes in membrane potential, changes in membrane geometry, ion redistribution, birefringence changes, etc. (see Hill D. K. and Keynes, R. D., "*Opacity Changes in Stimulated Nerve*," J. Physiol., Vol. 108, pp. 278-281 (1949); Foust A. J. and Rector D. M., "*Optically Teasing Apart Neural Swelling and Depolarization*," Neuroscience, Vol. 145, pp. 887-899 (2007)). Because fast-optical signals are associated with neuronal activity, rather than hemodynamic responses, fast-optical signals may be used to detect brain activity with relatively high temporal resolution.

Although traditional OCT and state of the art iNIRS systems are sufficient for their intended purposes, these techniques utilize holographic methods, mixing the detected light against a reference beam, thereby requiring a relatively complicated and expensive arrangement of components. Reference beams are notoriously challenging to keep stable in a stationary device, let alone a device that may be attached to a moving human body during operation, so a solution to this issue of stability is required to use OCT or iNIRS as a diagnostic tool. Further, while the iNIRS and OCT approaches are very sophisticated, they both require the detection and measurement of speckles, presenting challenges in a highly attenuating medium, such as the human body, due to the very low number of photons that reach each detector. Thus, a very large number of detectors (or pixels) are required to individually detect the speckles, thereby further increasing the complexity and expense of the system. This complexity and expense will, of course, be magnified as the OCT system or iNIRS system is scaled to increase the number of optical source-detector pairs for x-y (non-depth) spatial resolution.

There, thus, remains a need to provide a means for reducing the cost and complexity of an optical measurement system to non-invasively detect and localize a physiological event within an anatomical structure.

SUMMARY OF THE INVENTION

In accordance with a first aspect of the present inventions, a non-invasive optical measurement system comprises a two-dimensional array of photonic integrated circuits (PICs) mechanically coupled to each other. Each PIC is configured for emitting sample light into an anatomical structure (e.g., a brain), such that the sample light is scattered by the anatomical structure, resulting in physiological-encoded signal light that exits the anatomical structure. Each PIC is further configured for detecting the signal light.

In one embodiment, each of the PICs may comprise an optical waveguide, and an edge emitting optical source (e.g., a distributed feedback (DFB) laser)) that emits source light within the optical waveguide in a direction along a plane of the respective PIC, in which case, the sample light emitted by the respective PIC will be derived from the source light. In another embodiment, each of the PICs comprises an output port configured for emitting the respective sample light into the anatomical structure, and an input port configured for receiving the respective signal light from the anatomical structure. The output port and input port may be disposed on a planar surface of the respective PIC. In this case, the output port may be further configured for emitting the respective sample light into the anatomical structure in a direction perpendicular to a planar surface of the PIC, and the input port may be further configured for receiving the respective signal light from the anatomical structure from a direction perpendicular to the planar surface of the PIC.

The non-invasive optical measurement system may further comprise a controller configured for operating each of the PICs, such that each PIC detects the signal light created by the sample light emitted by the same PIC, operating each of the PICs, such that each PIC detects the signal light created by the sample light emitted by at least one different PIC, or operating each of the PICs, such that each PIC detects the signal light created by the sample light emitted from the same PIC and detects signal light created by the sample light emitted from at least one different PIC.

The non-invasive optical measurement system further comprises processing circuitry configured for analyzing the detected signal light from each of the PICs, and based on this analysis, determining an occurrence and a three-dimensional spatial location of a physiological event in the anatomical structure. Each of the PICs may comprise at least a portion of the processing circuitry. If the anatomical structure is a brain, the physiological event may be indicative of neural activity, e.g., a fast-optical signal. The processing circuitry may be configured for deriving optical path length information from the detected signal light from each of the PICs, and determining a spatial depth of the physiological event within the anatomical structure based on the optical path length information. For example, each of the PICs may be configured for varying an optical frequency of the emitted sample light (e.g., by sweeping the frequency of the emitted sample light), in which case, the processing circuitry may be configured for transforming the detected signal light for each of the PICs from a frequency domain representation into a time domain representation to obtain the optical path length information of the signal light. The processing circuitry may also be configured for determining the three-dimensional spatial location of the physiological event in the anatomical structure based on the geometric information defining locations of the PICs relative to each other.

In accordance with a second aspect of the present inventions, a non-invasive optical measurement method using a two-dimensional array of photonic integrated circuits (PICs) mechanically coupled to each other, comprises emitting sample light from each of the PICs into an anatomical structure (e.g., a brain), such that the sample light is scattered by the anatomical structure, resulting in physiological-encoded signal light that exits the anatomical structure. The optical measurement method further comprises detecting the signal light by each PIC.

In one method, the sample light is emitted from a planar surface of each of the PICs (e.g., in a direction perpendicular to the planar surface of each of the PICs), and the signal light is received at the planar surface of each of the PICs (e.g., in a direction perpendicular to the planar surface of each of the PICs). Each of the PICs may be operated, such that each PIC detects the signal light created by the sample light emitted by the same PIC, such each PIC detects the signal light created by the sample light emitted by at least one different PIC, or such that each PIC detects the signal light created by the sample light emitted from the same PIC and detects signal light created by the sample light emitted from at least one different PIC.

The non-invasive optical measurement method further comprises analyzing the detected signal light from each of the PICs, and determining an occurrence and a three-dimensional spatial location of the physiological event in the anatomical structure based on the analysis. If the anatomical structure is a brain, the physiological event may be indicative of neural activity, e.g., a fast-optical signal. The non-invasive optional measurement method may further comprise deriving optical path length information from the detected signal light from each of the PICs, and determining a spatial depth of the physiological event within the anatomical structure based on the optical path length information. For example, the non-invasive optical measurement period may comprise varying an optical frequency of the emitted sample light for each of the PICs (e.g., by sweeping the frequency of the emitted sample light), and transforming the detected signal light for each of the PICs from a frequency domain representation into a time domain representation to obtain the optical path length information of the signal light. The three-dimensional spatial location of the physiological event in the anatomical structure may also be determined based on the geometric information defining locations of the PICs relative to each other.

In accordance with a third aspect of the present inventions, a photonic integrated circuit (PIC) comprises a semiconductor substrate (e.g., silicon) configured for being disposed adjacent an anatomical structure, and an optical source monolithically integrated with the substrate. The optical source is configured for generating sample light.

In one embodiment, the PIC further comprises an optical waveguide monolithically integrated with the substrate. The first optical waveguide is optically coupled to the optical source for propagating the sample light within the substrate, in which case, the optical source may be an edge-emitting optical source (e.g., a distributed feedback (DFB) laser) configured for emitting the sample light within the optical waveguide in a direction along a plane of the substrate. In one embodiment, the PIC further comprises a waveform generator monolithically integrated with the substrate. The waveform generator may be configured for outputting an electrical drive signal, and the optical source may be electrically coupled to the waveform generator for receiving the electrical drive signal, such that the optical wavelength of the sample light is varied. In another embodiment, the PIC further comprises a temperature controller monolithically integrated with the substrate. The temperature controller may be configured for maintaining the optical source at a baseline operating temperature.

The PIC further comprises an output port and an input port (e.g., diffraction grating coupler) monolithically integrated with the substrate. The output port is optically coupled to the optical source for emitting the sample light into the anatomical structure, such that the sample light is scattered by the anatomical structure, resulting in physiological-encoded signal light that exits the anatomical structure. The input port configured for receiving the signal light from the anatomical structure. The signal light received by the input port may be created from the sample light emitted by the optical source of the same PIC or from sample light generated by an optical source of another PIC.

In one embodiment, the output port is configured for emitting the sample light into the anatomical structure from a planar surface of the substrate, and the input port is configured for receiving the signal light from the anatomical structure at the planar surface of the substrate. In this case, the output port may be configured for emitting the sample light into the anatomical structure in a direction perpendicular to the planar surface of the substrate, and the input port may be configured for receiving the signal light from the anatomical structure in a direction perpendicular to the planar surface of the substrate.

The PIC further comprises an optical detector monolithically integrated with the substrate. The optical detector is optically coupled to the input port for detecting physiological-encoded signal light and generating a physiological-encoded electrical signal. In one embodiment, the optical source is configured for generating the sample light by initially generating source light. In this case, the PIC may further comprise an optical beam splitter, optical delay line, and an optical beam combiner monolithically integrated with the substrate. The optical beam splitter may be optically coupled to the first optical waveguide for splitting the source light into the sample light and reference light; the optical delay line may be optically coupled to the optical beam splitter for delaying the propagation of the reference light; the optical beam combiner may be optically coupled to the input port and the optical delay line for combining the signal light and the reference light into an interference light pattern; and the optical detector may be optically coupled to the optical beam combiner for detecting the signal light within the interference light pattern.

In this case, the optical detector may be a balanced optical detector comprising an optical beam splitter configured for splitting the interference light pattern into a first and second phase-delayed interference light patterns, first and second pixel arrays for detecting the first and second phase-delayed interference light patterns, and an arithmetic unit for subtracting the first and second phase-modulated interference light patterns to extract an alternating current (AC) component of the interference light pattern. The signal light may be detected in the AC component of the interference light pattern. The PIC may further comprise another optical beam splitter and a normalizing optical detector monolithically integrated within the substrate. The other optical beam splitter may be configured for splitting the reference light into the reference light and normalizing light, and the normalizing optical detector may be configured for detecting the normalizing light and generating a normalizing electrical signal. The PIC may further comprise processing circuitry monolithically integrated with the substrate. The processing circuitry may be electrically coupled to the optical detector and the normalizing optical detector for normalizing the electrical signal based on the normalizing electrical signal.

In one embodiment, the PIC further comprises processing circuitry monolithically integrated with the substrate. The processing circuitry may be electrically coupled to the optical detector for processing the electrical signal. The electrical signal may comprise a plurality of optical frequencies, in which case, the processing circuitry may be configured for processing the electrical signal by transforming the electrical signal from a frequency domain representation to a time domain representation.

In accordance with a fourth aspect of the present inventions, a non-invasvie optical measurement method using a photonic integrated circuit (PIC) comprises emitting sample light from the PIC into the anatomical structure (e.g., a brain), such that the sample light is scattered by the anatomical structure, resulting in physiological-encoded signal light that exits the anatomical structure. The sample light may be emitted into the anatomical structure from a planar surface of the PIC (e.g., in a direction perpendicular to the planar surface of the PIC), and the signal light may be received from the anatomical structure at the planar surface of the PIC (e.g., in a direction perpendicular to the planar surface of the PIC). One method further comprises varying the optical wavelength of the sample light.

The non-invasive optical measurement method further comprises receiving physiological-encoded signal light from the anatomical structure at the PIC, and generating a physiological-encoded electrical signal. The signal light received by the PIC may be created from the sample light emitted by the PIC or may be created from sample light generated by another PIC. The non-invasive optical measurement method may further comprise maintaining the PIC at a baseline operating temperature. One method comprises generating the sample light within the PIC by initially generating source light, splitting the source light within the PIC into the sample light and reference light, delaying the propagation of the reference light within the PIC, and combining the signal light and the reference light into an interference light pattern within the PIC. In this case, the signal light may be detected within the interference light pattern. This optical measurement method may further comprise splitting the interference light pattern into a first and second phase-delayed interference light patterns within the PIC, detecting the first and second phase-delayed interference light patterns within the PIC, and subtracting the first and second phase-modulated interference light patterns within the PIC to extract an alternating current (AC) component of the interference light pattern. In this case, signal light may be detected in the AC component of the interference light pattern. This optical measurement method may further comprise splitting the reference light into the reference light and normalizing light within the PIC, detecting the normalizing light within the PIC, and generating a normalizing electrical signal within the PIC. The electrical signal may be normalized based on the normalizing electrical signal.

The method may further comprise processing the electrical signal. For example, the electrical signal may comprise a plurality of optical frequencies, in which case, processing the electrical signal may comprise transforming the physiologically-encoded electrical signal from a frequency domain representation to a time domain representation.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which:

FIGS. 3A and 3B are profile views of one embodiment of a photonic integrated circuit (PIC) for use in the wearable unit of FIG. 2, particularly illustrating the delivery of sample light into an anatomical structure and the detection of resulting signal light from the anatomical structure;

FIGS. 4A and 4B are profile views of another embodiment of PIC for use in the wearable unit of FIG. 2, particularly illustrating the delivery of sample light into an anatomical structure and the detection of resulting signal light from the anatomical structure;

FIG. 8A is an exemplary diagram of one chirped interference signal detected by a PIC used in the wearable unit of FIG. 2;

FIG. 8B is one time domain diagram of a chirped interference signal detected by the PIC used in the wearable unit of FIG. 2;

FIG. 8C is a time-averaged time domain diagram of a chirped interference signal detected by the PIC used in the wearable unit of FIG. 2;

DETAILED DESCRIPTION OF THE EMBODIMENTS

Figure 1:
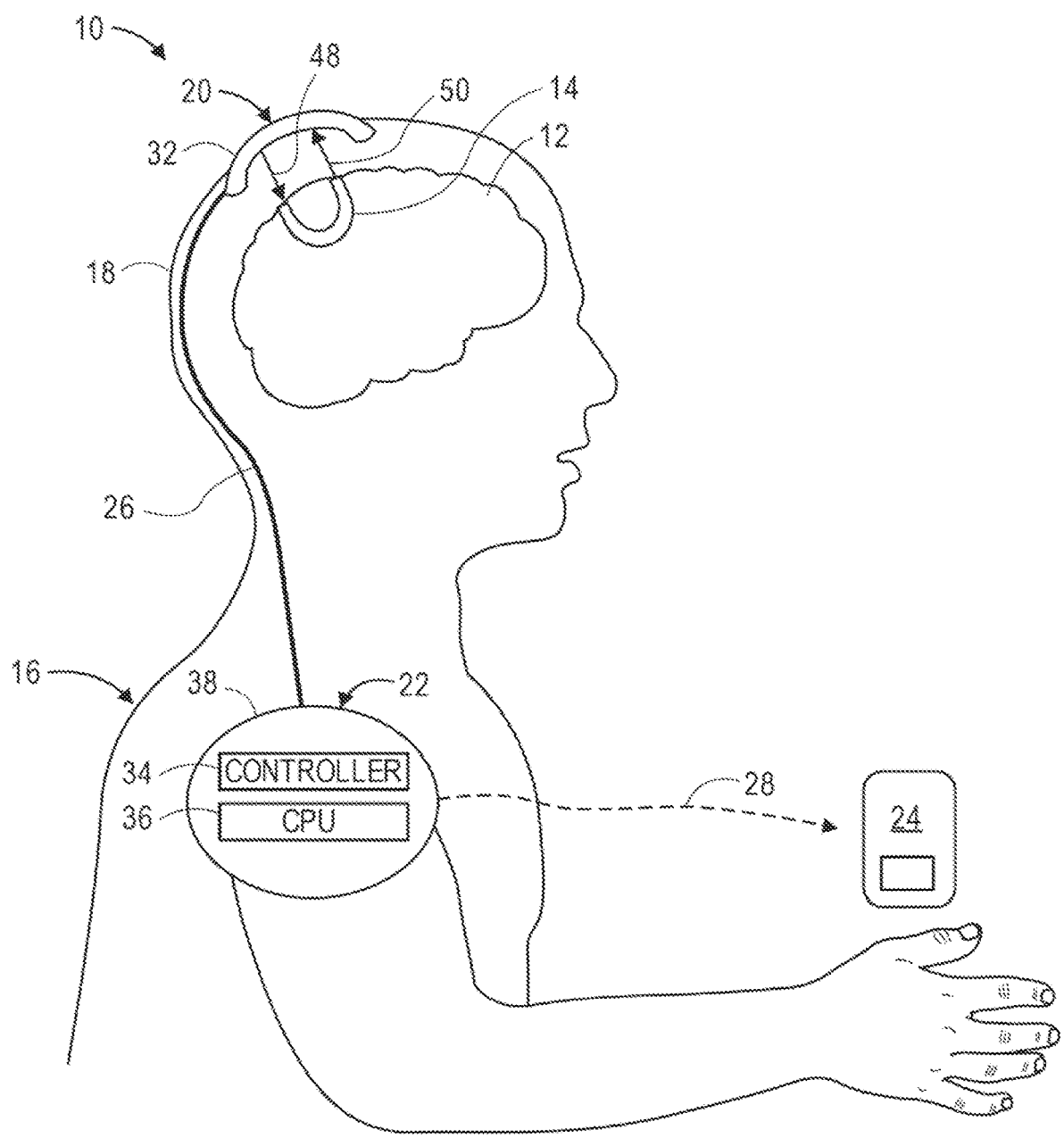
FIG. 1 is a plan view of a non-invasive optical measurement system constructed in accordance with one embodiment of the present inventions.

Referring first to FIG. 1, one embodiment of a non-invasive optical measurement system 10 constructed in accordance with the present inventions will now be described. The non-invasive optical measurement system 10 will be described as a swept-source holographic optical system (i.e., a system that mixes detected light against a reference beam in order to increase the signal-to-noise ratio (SNR) of the relevant signal), and in particular a Near-Infrared Spectroscopy (iNIRS) system. In alternative embodiments, the non-invasive optical measurement system 10 may take the form of other swept-source holographic optical systems, such as a Swept-Source Optical Computed Tomography (SS-OCT). In still other embodiments, the non-invasive optical measurement system 10 may take the form of a non-holographic optical system.

In any event, the non-invasive optical measurement system 10 is designed to non-invasively acquire physiological-encoded data (i.e., data representative of a physiologically-dependent optical parameter) in an anatomical structure 12 in order to detect and localize a physiological event in the anatomical structure 12. In the illustrated embodiments, the anatomical structure 12 is a brain. Although for exemplary purposes, the non-invasive optical measurement system 10 is described herein as being used to acquire physiological-encoded data from brain tissue, variations of the non-invasive optical measurement system 10 can be used to acquire physiological-encoded data from other anatomical structures of a human body, animal body and/or biological tissue.

In the illustrated embodiment, the non-invasive optical measurement system 10 detects a physiological event, such as a fast-optical signal, which refers to changes in optical scattering that occur when light propagating through active neural tissue (e.g., active brain tissue) is perturbed through a variety of mechanisms, including, but not limited to, cell swelling, cell volume change, changes in membrane potential, changes in membrane geometry, ion redistribution, birefringence changes, etc. Fast-optical signals are associated with neuronal activity, rather than hemodynamic responses, and fast-optical signals may be used to detect brain activity with relatively high temporal resolution. In alternative embodiments, the physiological event may be a slower hemodynamic change, e.g., Doppler shift due to moving blood flow, changes in blood volume, metabolism variations such a blood oxygen changes. As will be described in further detail below, the non-invasive optical measurement system 10, when properly tuned to a specific type of physiological event, is capable of decoding light propagating through the brain 12 to detect and localize that physiological event, and thus, may be alternatively or additionally tuned to detect any type of physiological event that causes a change in an optical property of the neural activity within the brain 12.

The neural activity information (or the acquired physiological-encoded data from which it is derived) may be transmitted to external programmable devices for use (e.g., computed, processed, stored, etc.) therein, e.g., medical devices, entertainment devices, neuromodulation stimulation devices, lie detection devices, alarm systems, educational games, brain interface devices, etc., and/or may be used internally to adjust the detection parameters of the non-invasive optical measurement system 10, such as increasing or decreasing the strength of the optical source and/or data compression and/or analysis, such a Fast Fourier Transform (FFT) and/or statistical analysis.

As will be appreciated from the following description, the non-invasive optical measurement system 10 utilizes photonic integrated circuit (PIC) technology to implement the iNIRS technique for detecting and localizing a physiological event in the brain 12. Furthermore, by integrating all optical components for each source-detector unit of the non-invasive optical measurement system 10 into a single PIC, such a unit can be miniaturized into a small and compact package, which, not only decreases the overall cost of the non-invasive optical measurement system 10, but also advantageously reduces sources of spurious optical and electronic noise, optical coupling losses, and sources of optical instability and inaccuracy, as compared to non-PIC implementations (e.g., imperfect optical fiber lengths, optical fiber movement, dispersion, etc.). The non-invasive optical measurement system 10 forms a modulator design, with the PIC forming the base unit, thereby enabling tiling of multiple PICs in parallel, which is more challenging to accomplish in a conventional optical measurement system. Thus, the utilization of PIC technology provides for a scalable and convenient means for detecting and localizing a physiological event over a large anatomical structure, such as the brain 12.

Referring still to FIG. 1, the non-invasive optical measurement system 10 includes a wearable unit 20 that is configured for being applied to the user 16, and in this case, worn on the head 18 of the user 16; an auxiliary head-worn or non-head-worn unit 22 (e.g., worn on the neck, shoulders, chest, or arm) coupled to the wearable unit 20 via a wired connection 26 (e.g., electrical wires); and an optional remote processor 24 in communication with the patient-wearable auxiliary unit 22 coupled via a wired connection 28 (e.g., electrical wires). Alternatively, the non-invasive optical measurement system 10 may use a non-wired connection (e.g., wireless radio frequency (RF) signals (e.g., Bluetooth, Wifi, cellular, etc.) or optical links (e.g., fiber optic or infrared (IR)) for providing power to or communicating between the respective wearable unit 20 and the auxiliary unit 22, and/or a wired connection between the auxiliary unit 20 and the remote processor 24.

Significantly, the optical functions (including optical sources, optical beam layout, and optical detectors), and optionally at least some of the control and/or processing functions, of the non-invasive optical measurement system 10 are fully integrated into a low-cost, high-volume, multifunctional platform using photonic integrated circuit (PIC) technology.

In particular, the wearable unit 20 is configured for acquiring a plurality of data from sample path 14, having a banana shape. The wearable unit 20 comprises a two-dimensional array of photonic integrated circuits (PICs) 30 (shown in FIG. 2) and a support structure 32 that carries the array of PICs 30 in a fixed relationship with each other. As will be described in further detail below, each PIC 30 performs interferometric-based detection of intensity and phase changes of the signal light 50 as a function of optical path length. The PIC 30 implements a specific type of interference detection in the frequency domain, where the frequency of the sample light 48 is varied as a function of time, as described below. The support structure 32 may be shaped, e.g., have a banana, headband, cap, helmet, beanie, other hat shape, or other shape adjustable and conformable to the user's head 18, such that the PICs 30 are in close contact with the outer skin of the body part, and in this case, the scalp of the user 16. An index matching fluid may be used to reduce reflection of the light generated by the PICs 30 from the outer skin of the scalp. An adhesive or belt (not shown) can be used to secure the support structure 32 to the head 18 of the user 16.

The auxiliary unit 22 comprises a controller 34, a central processing unit (CPU) 36, and a housing 38 containing the controller 34 and CPU 36. As will be described in further detail below, the controller 34 is configured for controlling the operational functions of the wearable unit 20, whereas the CPU 36 is configured for processing the physiological-encoded data acquired by the PICs 30 to ultimately determine the occurrence and three-dimensional location of a physiological event within the brain 12, although at least some of the processing of the physiological-encoded data may be performed by the PICs 30. The auxiliary unit 22 may additionally include a power supply (which if head-worn, may take the form of a rechargeable or non-chargeable battery), a control panel with input/output functions, a display, and memory. Alternatively, power may be provided to the auxiliary unit 22 wirelessly (e.g., by induction). The remote processor 24 may store image data from previous sessions, and include a display screen.

Any suitable memory can be used for the auxiliary unit 22. The memory can be a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal. The term "modulated data signal" can include a signal that has one or more of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display can be any suitable display device, such as a monitor, screen, or the like, and can include a printer. In some embodiments, the display is optional. In some embodiments, the display may be integrated into a single unit with the remote processor 24, such as a tablet, smart phone, or smart watch. The input device can be, for example, a keyboard, mouse, touch screen, track ball, joystick, voice recognition system, or any combination thereof, or the like.

Although the controller 34 and processor 36 are described herein as being separate components, it should be appreciated that portions or all functionality of the controller 34 and processor 36 may be performed by a single computing device. Furthermore, although all of the functionality of the controller 34 is described herein as being performed by a single device, and likewise all of the functionality of the processor 36 is described herein as being performed by a single device, such functionality each of the controller 34 and the processor 36 may be distributed amongst several computing devices. Moreover, it should be appreciated that those skilled in the art are familiar with the terms "controller" and "processor," and that they may be implemented in software, firmware, hardware, or any suitable combination thereof.

Figure 2:
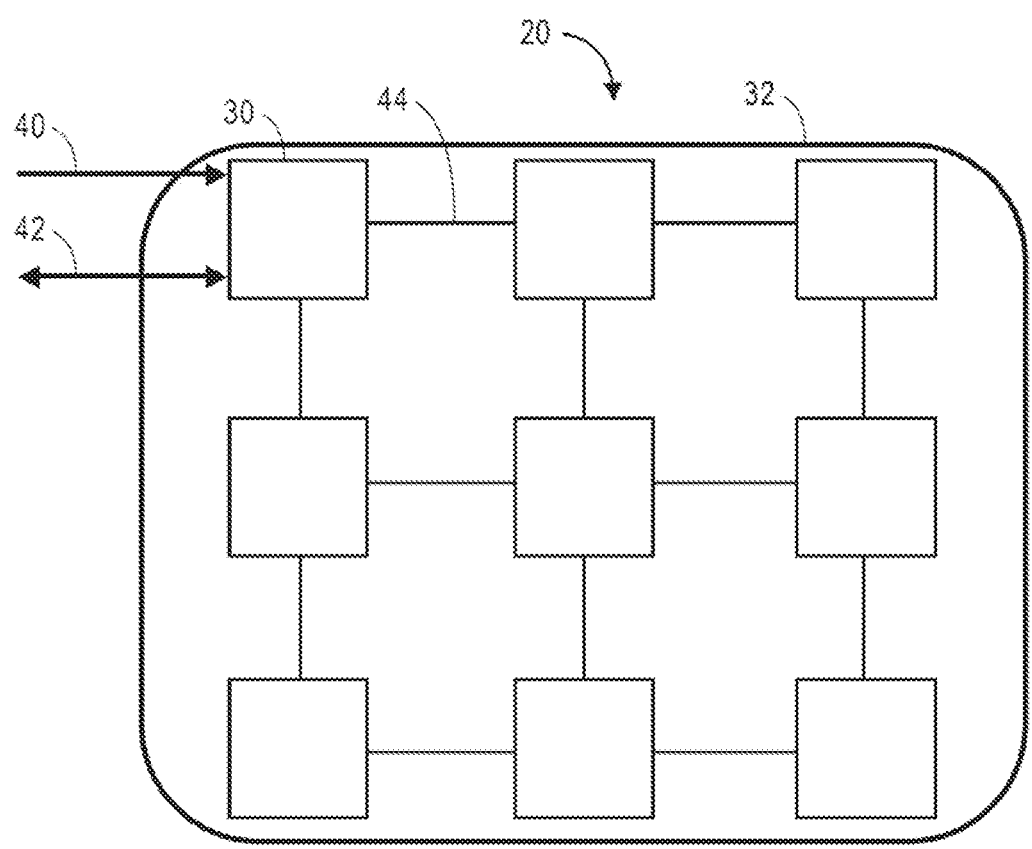
FIG. 2 is a plan view of one embodiment of a wearable unit used in the non-invasive optical measurement system of FIG. 1.

As shown in FIG. 2, the wearable unit 20 comprises a 3×3 array of PICs 30, although other dimensions for the array of PICs 30 can be provided, e.g., 2×2, 4×4, 2×3, etc., depending upon the particular application and needs of the non-invasive optical measurement system 10. The wearable unit 20 further comprises a power conduit 40 configured for providing power to the PICs 30 from the auxiliary unit 22, and a data input/output conduit 42 configured for providing control/measurement data between the PICs 30 and the auxiliary unit 22. The PICs 30 may, themselves, be electrically coupled to each other via electrical conduits 44, such that relevant data (e.g., optical path length-dependent intensity and phase data described in further detail below) can be communicated between the PICs 30.

Referring now to FIGS. 3A and 3B, each of the PICs 30 is configured for being placed adjacent to the head 18 of the user 16 and emitting sample light 48 into the brain 12, which is scattered by the brain 12, resulting in the physiological-encoded signal light 50 that exits the brain 12. In particular, the sample light 48 first passes through the scalp 52a, skull 52b, and cerebral spinal fluid (CSF) 52c along a relatively straight path, enters the brain 12, then exits in reverse fashion along a relatively straight path through the CSF 52c, skull 52b, and scalp 52a, thereby defining a banana-shaped optical path 14.

As it scatters diffusively through the brain 12, various portions of the sample light 48 will take different paths through the brain 12. For purposes of brevity, only a first sample light portion 48a traveling along a relatively short path, and a second sample light portion 48b traveling along a relatively longer path, are illustrated, although it should be appreciated that the diffused sample light 48 will travel along many more paths through the brain 12. Thus, the sample light 48 will reflect off of the brain 12 at different depths (corresponding to the different optical path lengths), and exit as the signal light 50 that is subsequently detected.

Significantly, the signal light 50 will be encoded with any physiological events that change an optical property of tissue within the brain. The non-invasive optical measurement system 10, when properly tuned to a specific type of physiological event is capable of decoding the signal light 50 to detect and localize that physiological event. To this end, each PIC 30 is further configured for detecting the physiological-encoded signal light 50 and generating a physiological-encoded electrical signal from which an occurrence and a three-dimensional spatial location of the relevant physiological event in the brain 12 can be determined, as will be described in further detail below. It should be appreciated that, although not all of the sample light 48 from which the signal light 50 is derived passes through the brain 12 and is detected, it is only important that at least some of the signal light 50 exiting the brain 12 be detected.

The sample light 48, and thus the signal light 50, may be ultraviolet (UV) light, visible light, and/or near-infrared and infrared light, and may have any suitable wavelength, e.g., in the range of 350 nm-1800 nm. In accordance with the iNIRS technique, each PIC 30 is configured for varying the optical wavelength (i.e., the frequency) of its respective sample light 48 over time across a defined wavelength range, e.g., by rapidly sweeping (or "chirping") the optical wavelength of the sample light 48 from the low end of the wavelength range to the high end of the wavelength range, or vice versa. Such defined optical wavelength range will typically be narrow, e.g., 20 nm.

It is preferred that the range of optical wavelengths through which the sample light 48 is swept for each PIC 30 be selected to maximize sensitivity to the specific physiological event of interest. For example, in the preferred case where the physiological event of interest is the presence of a fast-optical signal, a center optical wavelength greater than 850 nm may be used for the sample light 48. Optionally, a center optical wavelength equal to or greater 1000 nm may be used for the sample light 48 to maximize penetration. In the additional or alternative case where the physiological event of interest is a change in the blood oxygen concentration, a center optical wavelength in the range of 650 nm to 750 nm may be used for the sample light 48. Multiple optical wavelengths can be used for the sample light 48 to allow different physiological events to be distinguished from each other. For example, sample light 48 having two center optical wavelengths of 900 nm and 700 nm can be respectively used to resolve fast-optical signals and blood oxygenation.

Notwithstanding the foregoing, the PIC 30 described herein operates best with near-infrared light (approximately 1550 nm), and therefore, lends itself well to the detection of fast-optical signals. However, the PIC 30 may also operate at another near-infrared wavelength (e.g., at 1064 nm or 850 nm), or even at visible light (e.g., at 750 nm) if suitable materials other than silicon are used in the PIC 30 to allow propagation of the visible light.

Light can be coupled between the PIC 30 and the brain 12 in any variety of manners. For example, as illustrated in FIGS. 3A and 3B, the PIC 30 comprises an output port 54*a* (associated with an optical source as will be described in further detail below) from which the sample light 48 is coupled directly into the brain 12, and an input port 54*b* (associated with detector as will be described in further detail below) into which the signal light 50 is coupled directly from the brain 12. Both of the output port 54*a* and input port 54*b* may take the form of grating couplers disposed directly on the same planar surface of the PIC 30. In this case, the PIC 30 will be placed directly against, or in very close proximity to, the scalp 52 of the head 18, such that the light exiting or entering the grating couplers 54*a*, 54*b* directly enter or exit the head 18 from or into the PIC 30. In this embodiment, the sample light 48 is emitted from the plane of the respective PIC 30 (as well as the plane of the support structure 32), preferably, in a direction perpendicular to the plane of the PIC 30 (as well as the plane of the support structure 32), such that it is directed towards the brain 12, and the signal light 50 is received at the plane of the respective PIC 30 (as well as the plane of the support structure 32), preferably, in a direction perpendicular to the plane of the PIC 30 (as well as the plane of the support structure 32), such that it is received from the brain 12.

As illustrated in FIGS. 4A and 4B, the ports 54*a*, 54*b* may be respectively extended from the grating couplers using optical fibers 56*a*, 56*b*, thereby freeing up the requirement that the PIC 30 be disposed directly on the surface of the head 18. In this case, the sample light 48 is coupled from the PIC 30 into the optical fiber 56*a* via the output port 54*a*, and the signal light 50 is coupled from the optical fiber 56*b* into the PIC 30 via the input port 54*b*. As depicted in FIGS. 3A and 4A, the greater distance of the optical path 14 may be across the x-y plane as compared to its distance along the z-direction. Thus, the shape and size of the optical path 14 will be defined by the location of the output port 54*a* and the location of the input port 54*b* (or the distal ends of the optical fibers 56*a*, 56*b*).

Although the controller 42 is configured for operating each of the PICs 30 to detect the physiological-encoded signal light 50 in response to the sample light 48 emitted by the same PIC 30, as illustrated in FIGS. 3A-3B and 4A-4B, the controller 42 can be configured for operating each of the PICs 30 to detect the physiological-encoded signal light 50 in response to the sample light 48 emitted by at least one different PIC 30, thereby defining additional optical paths 14 and increasing the spatial resolution of the non-invasive optical measurement system 10.

Figure 5:
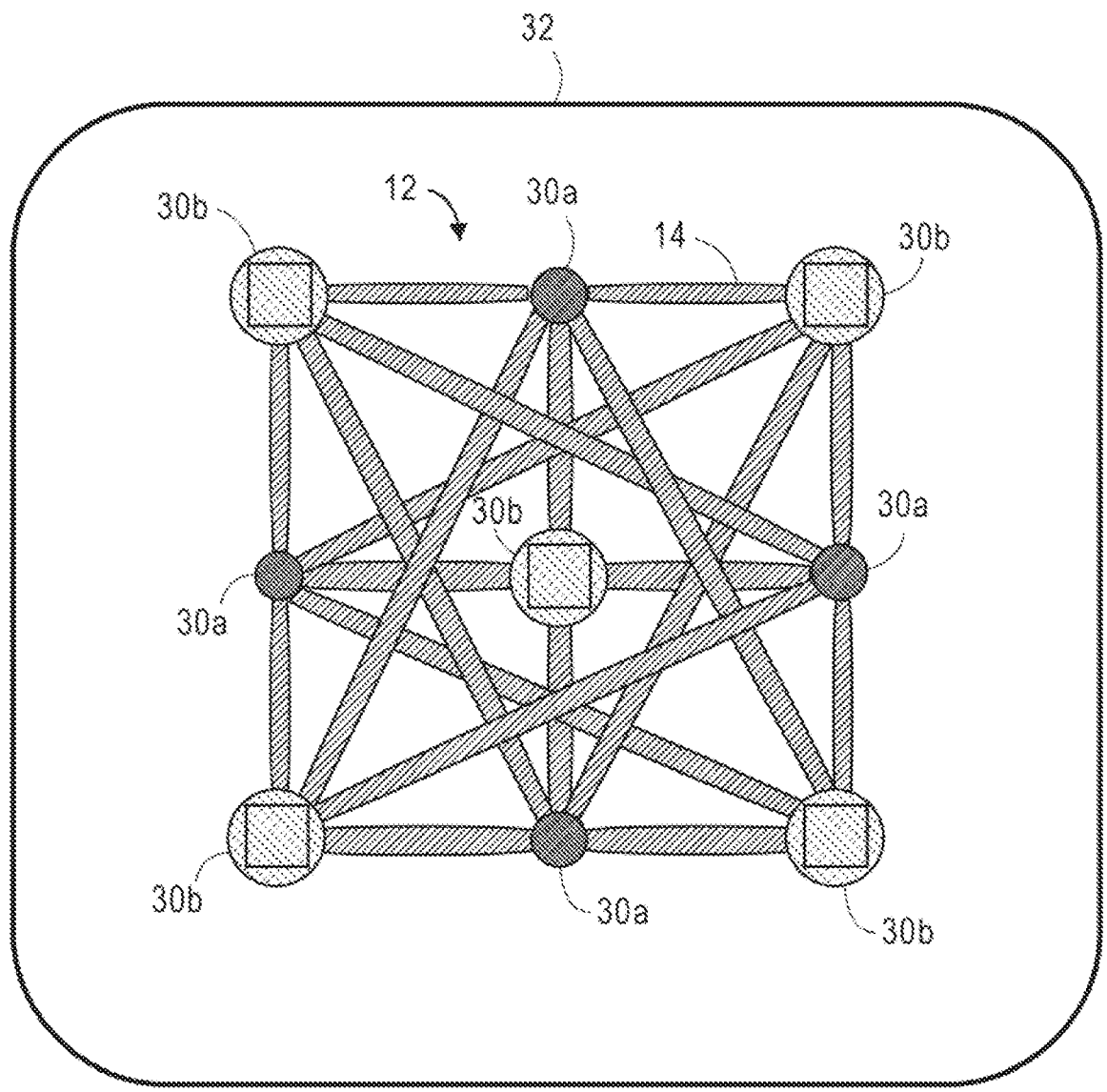
FIG. 5 is a plan view illustrating an arrangement of plan view of a wearable unit used in the non-invasive optical measurement system of FIG. 1, particularly illustrating the creation of optical paths between the PICs.

For example, as illustrated in FIG. 5, some of the PICs 30 may serve as dedicated optical sources 30*a*, and others of the PICs 30 may serve as dedicated optical detectors 30*b*, such that multiple optical paths 14 are acquired between the dedicated optical sources and dedicated optical detectors. That is, each optical path 14 is defined by a given optical source 30*a* at a given location and a given optical detector 30*b* at a given location. Thus, the optical sources 30*a* and optical sources 30*b* are located at fixed positions. In effect, this creates multiple paired source-detector combinations between various permutations of the optical sources 30*a* and optical detectors 30*b*, and thus, many more optical paths 14 through the brain 12 within a single measurement period, as compared to the embodiment illustrated in FIG. 3. That is, the number of optical paths 14 defined per each measurement period in the embodiment illustrated in FIG. 3 equals the number N of PICs 30, whereas the number of optical paths 14 acquired per each measurement period in the embodiment illustrated in FIG. 5 can be N!.

Since each PIC 30 may serve as either an optical source 30*a* or as an optical detector 30*b* at any given time, the arrangement of optical sources 30*a* and optical detectors 30*b* may be dynamically changed over time via the controller 34 (described in further detail below). Alternatively, certain ones of the PICs 30 may be dedicated to emitting sample light 48, in which case, such PICs 30 may only be operated as optical sources 30*a*, and others of the PICs 30 may be dedicated to detecting signal light 50, in which case, such other PICS 30 may only be operated as optical detectors 30*b*.

In the embodiment illustrated in FIG. 5, four PICs serve as the optical sources 30*a* (four on the sides), and five PICs serve as optical sources 30*a* (four on the corners and one in the center). However, the optical sources 30*a* and optical detectors 30*b* may be arranged or located in a symmetric or asymmetric array and/or may be arranged in a circular or radial pattern or a rectangular-shaped pattern. The fields of view of the optical sources 30*a* and optical detectors 30*b* with respect to each other may have areas of overlap and/or may have little or no overlap. In some variations, the optical sources 30*a* and optical detectors 30*b* may be tiled on the support structure 32 adjacent to each other, such that the individual fields-of-view are adjacent to each other with little or no overlap.

The aggregate of the individual fields-of-view may simulate a single camera with a large field-of-view. Thus, the definition of multiple optical paths 14 may facilitate the generation of a high-resolution functional map of the upper layer of cortex of the brain 12 with spatial resolution given by the x-y plane (i.e., along the plane of the scalp 52*a*) confinement of the paths, in the manner of tomographic volume reconstruction. Moreover, a region of interest is probed with multiple wavelengths of light (i.e., multiple frequencies). This enables the detection of optical information about multiple optical paths 14 between each optical source 30*a* and pre-determined locations of the multiple optical detectors 30*b*, allowing optical paths 14 from the pre-determined location at the origin of the respective optical source 30*a* to be defined along multiple axes. Optical paths 14 defined along multiple axes across a region of interest may facilitate the generation of a 3-D map of the region of interest. Optical paths 14 defined by the optical detectors 30*b* may be used to detect neural signals with comparable resolution in the z-direction (i.e., perpendicular to a scalp 40 as in the x-y plane (i.e., along the scalp 40), and/or may allow optical probing or interrogation of larger region in brain 12 (e.g., across multiple optical paths 14 over a surface of the scalp 52a), and/or may improve the fidelity of the measured signal (i.e., the signal-to-noise) from a particular brain region of interest (e.g., from deeper depth within the cortex of the brain).

Although the controller 42 is configured for operating each of the PICs 30 as either dedicated optical sources or dedicated optical detectors, the controller 42 may be configured for operating each of the PICs 30 to detect the physiological-encoded signal light 50 in response to the sample light 48 emitted by the same PIC 30 and at least one other different PIC 30.

Regardless of the nature in which the controller 42 operates each of the PICs 30 (either an optical source, optical detector or both), one or more of the PICs 30 may be movable relative to the support structure 32 to defined even more optical paths 14, as described in U.S. Provisional Patent Application Ser. No. 62/692,074, entitled "Frequency Domain Optical Spectroscopy For Neural Decoding," and U.S. patent application Ser. No. 16/379,090, entitled "Non-Invasive Frequency Domain Optical Spectroscopy For Neural Decoding," which is expressly incorporated herein by reference.

Figure 6:
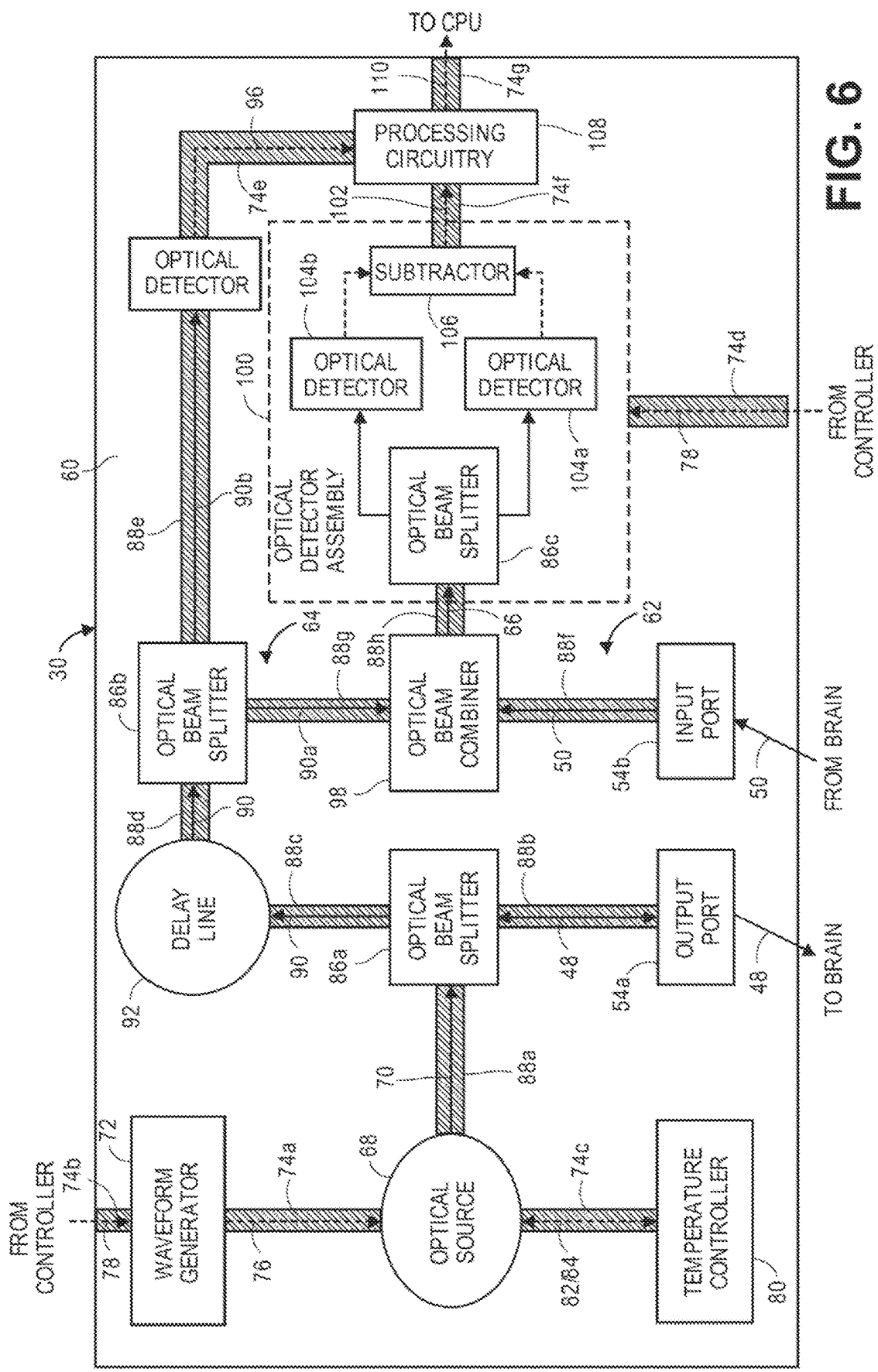
FIG. 6 is a block diagram of the detailed componentry of one embodiment of a PIC for use in the wearable unit of FIG. 2.

Referring now to FIG. 6, one embodiment of a PIC 30 that can be used in the wearable unit 20 of FIG. 2 will be described in further detail. The PIC 30 comprises a semiconductor substrate 60 (e.g., silicon) on which various optical and electrical components are monolithically integrated into a single package. Thus, the PIC 30 provides for a fully integrated optical source, interference componentry, and detector all on a PIC 30. The PIC 30 may be manufactured using thin-film technology, i.e., by depositing a thin film of material over a substrate or onto previously deposited layers.

As described above, the PIC 30 comprises an output port 54a (e.g., in the form of a diffraction grating coupler) configured for emitting the sample light 48 into the brain 12, and an input port 54b (e.g., in the form of a diffraction grating coupler) configured for receiving the physiological-encoded signal light 50 from the brain 12.

In the illustrated embodiment, the PIC 30, at least in part, functions as an interferometer, for example a Mach-Zehnder type interferometer, and comprises a sample arm 62 that passes through the brain 12 and a reference arm 64 that operate together to create at least one interference light pattern 66. When frequency of the sample arm and reference arm light are swept (i.e., varied linearly from one starting frequency to a different ending frequency), it is well known that the resulting interference pattern will exhibit a beat pattern representative of the signal light 50. In the illustrated embodiment, each of the interference light pattern(s) 66 takes the form of a speckle light pattern, which can be defined as an intensity pattern produced by the mutual interference of a set of scattered wavefronts. That is, a speckle light pattern results from the interference of many waves, but having different phases and amplitudes, which add together to give a resultant wave whose amplitude, and therefore intensity and phase, varies randomly.

The non-invasive optical measurement system 10 comprises an optical source 68 configured for generating source light 70 from which the afore-described sample light 48 is derived, as will be described in further detail below. In the preferred embodiment, the optical source 68 takes the form of a distributed feedback (DFB) laser, although in other embodiments, the optical source 68 may take the form of a highly coherent vertical cavity surface emitting laser (VCSEL), distributed Bragg reflector (DBR) laser, a Fourier domain mode locked (FDML) laser, etc. However, the non-invasive optical measurement system 10 leverages the fact that iNIRS, as opposed to other implementations that require optical sources with higher constraints (e.g., a VCSEL or FDML lasers), is capable of operating well with a DFB laser, which provides for a much longer coherence length for the source light 70, and thus the sample light 48, thereby providing for a much more stable and high-contrast interference light pattern 66. Furthermore, the use of a DFB laser, or other types of edge-emitting lasers, such as the DBR laser, allows the optical source 68 to be more easily incorporated into the PIC 30, since the source light 70 will be emitted within an optical waveguide formed within the substrate 60 in a direction along the plane of the PIC 30 (i.e., parallel to the planar surface of the PIC 30), as will be described in further detail below. This should be contrasted with surface-emitting lasers (e.g., VCSEL or FDML lasers), which emit source light in a direction perpendicular to the planar surface of the PIC 30, making it much difficult to implement in the PIC 30.

As will be described in further detail below, the DFB laser comprises an optical cavity having a diffraction grating that serves as a wavelength selective element and provides optical feedback that reflects light back into the cavity to form the resonator.

The grating is constructed so as to reflect only a narrowband of wavelengths, and thus produce a single longitudinal lasing mode. Altering the temperature of the DFB laser causes the pitch of the grating to change due to the dependence of refractive index on temperature, thereby altering the wavelength of the output, thereby making the DFB laser tunable on the order of 6 nm for a 50° K change in temperature. Altering the current powering the DFB laser causes a temperature change inside of the DFB laser, thereby allowing it to be tuned in a controlled manner. In one exemplary embodiment, the central wavelength of the DFB laser may be in the range of 600 nm-900 nm with a tunable frequency of 10 GHz and the frequency of the DFB laser may be swept within (i.e., a 1 MHz chirp repetition rate).

Figure 7A:
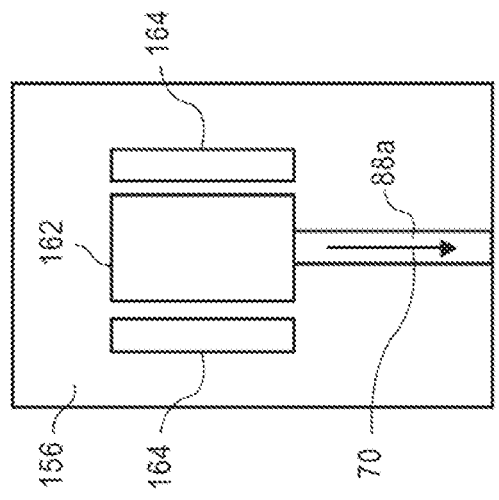
FIG. 7A is one profile view of a distributed feedback (DFB) laser incorporated into the PIC of FIG. 6.
Figure 7B:
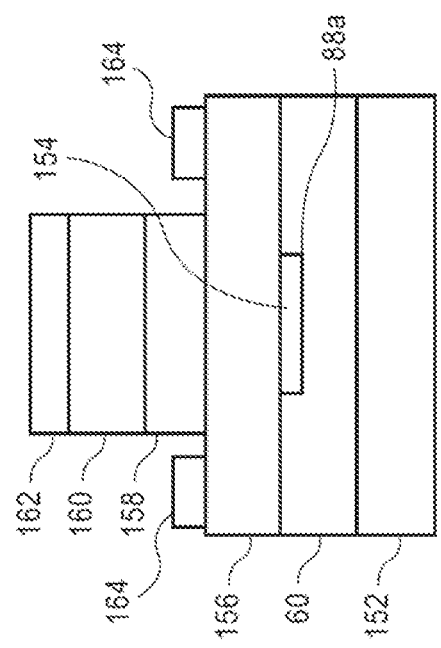
FIG. 7B is a plan view of DFB laser of FIG. 7A.
Figure 7C:
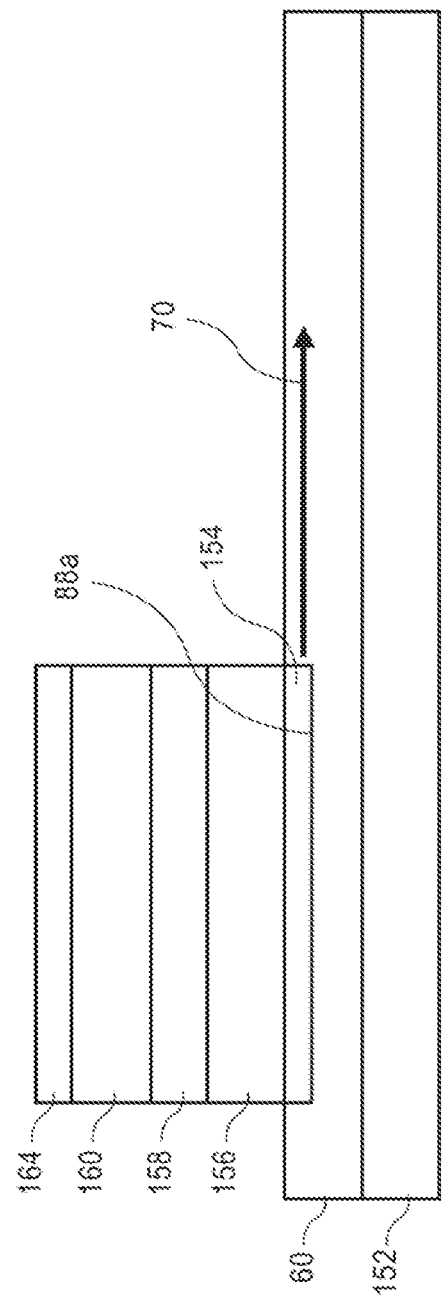
FIG. 7C is another profile of the DFB laser of FIG. 7A.

In the illustrated embodiment, the DFB laser can be, e.g., a Hybrid Silicon/III-V laser that is integrated on the silicon substrate 60. For example, referring to FIGS. 7A-7C, one embodiment of a DFB laser 68 will now be described. The optical waveguide 88a (as well as the optical waveguides 88b-88h) takes the form of a channel formed within a small portion of the silicon substrate 60, and through which the source light 70 propagates. A silicon oxide insulator layer 152 is disposed on the opposite side of the substrate 60. The DFB laser 68 further comprises a resonator structure 154 disposed in the optical waveguide 88a. The resonator structure 154 comprises a periodic structure that acts as a distributed reflector in the wavelength range of the source light 70. The DFB laser 68 further comprises an N-type layer 156 disposed on the surface of the silicon substrate 60 above the resonator structure 154, an active region 158 (e.g., multiple quantum wells) disposed on the N-type (N-doped) layer 156, and a P-type (P-doped) layer 160 disposed on the active region 158. The active region 158, N-type region 156 and P-type region 160 are composed of a suitable semiconductor material, such as, e.g., GaAs or InGaAs. The DFB laser 68 further comprise an N-type contact 162 disposed on the P-type layer 160 and two P-type contacts 164 disposed on the N-type layer 156 on opposite sides of the active region 158. Thus, the drive signal 76 from the wave generator 72 can be applied across the N-type contact 162 and P-type contacts 164 to pump the DFB laser 68 via the active region 158. The resulting source light 70 is emitted from the resonator structure 154 along the optical waveguide 88*a* in a direction parallel to the surface of the silicon substrate 60. It should be noted that, although the resonator structures of typical DFB lasers typically reside within the active regions of such lasers (i.e., where the photons are generated), the resonator structure 154 of the DFB laser 68 illustrated in FIGS. 7A-7C is directly beneath the active region 158 in the substrate 60 where the photons will propagate into the optical waveguide 88*a*.

Referring back to FIG. 6, the PIC 30 further comprises a waveform generator 72 electrically coupled to the optical source 68 via an electrical conduit 74*a* (e.g., one or more electrical traces), and is configured for outputting an electrical drive signal 76, which drives the optical source 68. The drive signal 76 may be sinusoidal and may have a suitable frequency of, e.g., 50 KHz-250 MHz. The waveform generator 72 may receive control signals 78 from the controller 34 (either analog or direct digital synthesis inputs) via an electrical conduit 74*b* (e.g., one or more electrical traces) for modulating the intensity of the drive signal 76, thereby varying the operating temperature of the optical source 68, and thus, the wavelength of the sample light 48 output from the optical source 68. The intensity of the drive signal 76 may be gradually increased or decreased to sweep the optical wavelength of the sample light 48 from low to high or from high to low using sawtooth, triangle or sinusoidal driving waves, for example. Alternatively, the drive signal 76 may take the form of a short electrical pulse that "rings" the optical source 68, thereby sweeping the optical wavelength from low to high or from high to low.

The PIC 30 further comprises a temperature controller 80 electrically coupled to the optical source 68 via an electrical conduit 74*c* (e.g., one or more electrical traces), and is configured for maintaining the optical source 68 at a baseline operating temperature, such that the actual optical wavelength range of the source light 70 (and thus the sample light 48) does not vary substantially from the nominal optical wavelength range of the source light 70. That is, the optical source 68 may generate a relatively high amount of heat that, without temperature control, would change the "chirp" (or frequency-time curve) of the source light 70, thereby causing sampling of the signal light 50 at inconsistent frequencies. The temperature controller 80 may comprise a passive heat sink (e.g., fins) (not shown) thermally coupled to the optical source 68, or an active heat sink whose temperature is varied through the thermoelectric effect via an electrical current. The temperature controller 80 senses the instantaneous temperature of the optical source 68 via sensing signals 82 and injects a current 84 to heat the optical source 68 if the sensed temperature drops below a threshold temperature, or cool the optical source if the sensed temperature exceeds a threshold temperature.

In an alternative embodiment, the temperature controller 80 may be electrically coupled to the optical source 68 via a temperature-variable "chip" (not shown) that is attached directly to the optical source 68. The temperature-variable chip may be heated/cooled via the thermoelectric effect (in response to a control signal sent by the temperature controller 80).

The PIC 30 further comprises an optical beam splitter 86*a* optically coupled to the output of the optical source 68 via an optical waveguide 88*a*, and is configured for splitting the source light 70 into the sample light 48, which propagates along an optical waveguide 88*b* of the sample arm 62 of the interferometer to the output port 54*a*, and reference light 90, which propagates along an optical waveguide 88*b* of the reference arm 64 of the interferometer. The optical beam splitter 86*a* may not necessarily split the source light 70 equally into the sample light 48 and reference light 90, and it may actually be more beneficial for the optical beam splitter 86*a* to split the source light 70 unevenly, such that the intensity of the sample light 48 is less than the intensity of the reference light 90 (e.g., 99/1 power ratio), since much of the sample light 48 will be lost after passing through the brain 12. That is, the intensity of the sample light 48 should be boosted relative to the reference light 90 to compensate for the losses incurred by the sample light 48 as it passes through the brain 12 and the fact that only a small portion of the signal light 50 exiting the brain 12 will enter the input port 54*b*.

The PIC 30 further comprises an optical delay line 84 optically coupled to the output of the optical waveguide 88*c* for delaying the propagation of the reference light 90, such that the length of the reference arm 64 (i.e., the optical path length of the reference light 90) matches the nominal optical path length of the sample arm 62 (i.e., the optical path length of the sample light 48). The optical length of the delay line 84 may be relatively long, e.g., 30 cm.

The PIC 30 further comprises an optical beam splitter 86*b* optically coupled to the output of the optical delay line 62 via an optical waveguide 88*d*, and is configured for splitting the reference light 90 into first reference light 90*a* and second reference light 90*b*. In the illustrated embodiment, the optical beam splitter 86*b* splits the reference light 90 equally (i.e., 50/50 power ratio), although it should be appreciated that the optical beam splitter 86*b* may not necessarily split the reference light 90 equally into the first reference light 90*a* and second reference light 90*b*.

The PIC 30 further comprises a normalizing optical detector 94 optically coupled to the one output of the optical beam splitter 86*b* via an optical waveguide 88*e*, and is configured for detecting the second reference light 90*b* (indicative of fluctuations in the intensity of the source light 70 as a function of time) and outputting a normalizing electrical signal 96, which as will be described in further detail below, will be used to normalize the physiological-encoded signal light 50. The optical detector 94 may take the form of a very simple and inexpensive single component (e.g., a photodiode).

The PIC 30 further comprises an optical beam combiner 98 optically coupled to the input port 54*b* via an optical waveguide 88*f*, and is coupled to the other output of the optical beam splitter 86*b* via an optical waveguide 88*g*, and is configured for combining the physiological-encoded signal light 50 and the first reference light 90*a* via superposition to generate the interference light pattern 66.

The PIC 30 further comprises an optical detector assembly 100 optically coupled to the output of the optical beam combiner 98 via an optical waveguide 88*h*, and is configured for detecting the physiological-encoded signal light 50 within the interference light pattern 66, and outputting a physiological-encoded electrical signal 102. In the illustrated embodiment, the optical detector assembly 100 takes the form of a balanced optical detector that splits interference light pattern 66 via an optical beam splitter 86*c* into two phase-modulated interference light patterns that are out of optical phase by 180 degrees, detects the phase-modulated interference light patterns on two different detectors 104*a*, 104*b*, subtract the two phase-modulated interference light patterns via an arithmetic unit 106 (e.g., a subtractor) to remove the DC component from the interference light pattern 66 and obtain the AC component of the interference light pattern 66 (i.e., to extract the beat pattern (as the amplified signal light 50) from the interference light pattern 66), and digitally outputs the physiological-encoded electrical signal 102 in the form of positive and negative intensity values, which are ambiguous due to the complex conjugate of the electrical signal 102, but from which the intensity values and phases values for the respective speckle grains can be derived.

Each of the detectors 104a, 104b of the optical detector assembly 98 may be composed of, e.g., silicon doped with germanium. Each detector 104a, 104b includes an array of one or more pixels, which is configured for simultaneously detecting the spatial components of the interference light pattern 66. In the case where the interference light pattern 66 is a speckle light pattern, the spatial components are speckle grains (approximately the size of a wavelength of the light) of the speckle light pattern. In this case, the positive and negative intensity values of the physiological-encoded electrical signal 102 output by optical detector assembly 100 comprises an array of positive or negative intensity values.

The optical detector assembly 100 includes control inputs (not shown) for receiving control signals 78 from the controller 34 via an electrical conduit 74d (e.g., one or more electrical traces), such that detection of the spatial components of the interference light pattern 66 can be coordinated with the delivery of the sample light 48 into the brain 12, and further can be operated to sample the interference light pattern 66 at various times throughout each optical wavelength sweep of the sample light 48. For example, if the sampling rate of the optical detector assembly 100 is 100 MHz, and the chirp repetition rate of the optical source 68 is 1 MHz, then the optical detector assembly 100 will obtain one hundred values for the physiological-encoded electrical signal 102 for each paired pixel of the optical detector assembly 100 (i.e., each pair of corresponding pixels on the detectors 104a, 104b).

Although not illustrated, the PIC 30 may include magnification optics and/or apertures to magnify the individual speckle grains, which may have a size on the order of the wavelength of the near-infrared or visible light used to acquire the data, and hence on the order of hundreds of nanometers in size, to approximately the sizes of the pixels of the optical detector assembly 100. Thus, in the illustrated embodiment, the pixel sizes and pitches of the optical detector assembly 100 are matched to the speckle grain sizes and pitches of the speckle light pattern 66 via the appropriate magnification, although other embodiments are possible.

The PIC 30 further comprises processing circuitry 108 (e.g., an application specific integrated circuitry (ASIC)) electrically coupled to the outputs of the normalizing optical detector 94 and optical detector assembly 100 respectively via electrical data busses 74e, 74f (e.g., one or more electrical traces), and is configured for normalizing the physiological-encoded electrical signal 102 based on the normalizing electrical signal 96. That is, any fluctuations in the designed waveform of the sample light 48 caused by tolerances in the optical source 68 may be removed from the physiological-encoded electrical signal 102. Thus, the processing circuitry 108 is configured for outputting normalized physiological-encoded data 110 to the CPU 36 via an electrical conduit 74g (e.g., one or more electrical traces).

The normalized physiological-encoded data 110 may comprise raw normalized intensity and phase values (i.e., a complex frequency spectrum measurement (intensity and phase) of the detected signal light 50 over the defined optical wavelength range of the sample light 48) or may comprise additionally processed data. For example, the processing circuity 108 may perform additional processing functions on the digitized physiological-encoded data 110, including computing and outputting relevant data of interest (e.g., intensity-optical path length information of the signal light 50 (i.e., a measure of the intensity of the detected signal light as a function of optical path length)) as the physiological-encoded data 110.

To this end, the processing circuitry 108 may compute a set of intensity values and phase values (respectively corresponding to the paired pixels of the optical detector assembly 92, i.e., one intensity value and one phase value for each paired pixel) from each sampled value of the physiological-encoded electrical signal 102. That is, for each paired pixel, a single intensity value and a single phase value will be associated with each sampled frequency of the sample light 48. The processing circuitry 108 may be configured for computing and storing a mean of the intensity values and phase values over the pixels in memory (not shown) for each sampled frequency. The phase may be measured by assigning a phase to the detected intensity of the signal light 50 versus time curve with respect to the phase of the sample light 48 for each optical wavelength). The processing circuitry 108 may also be configured for storing physiological-encoded data 110 (e.g., multiple mean intensity values and phase values) over several measurement periods (e.g., 100 mean intensity values and phase values)) in the memory for each sampled frequency.

In one measurement technique, the processing circuitry 108 will detect exemplary time domain information 112 for every chirp interval, consisting of chirped interference values detected over one chirp interval, as illustrated in FIG. 8A. Each set of time domain measurements per chirp interval may be Fourier transformed into a sequence of complex values 114 that represent the amplitude and phase of the detected signal light 50 as a function of optical path length (here, only the magnitude of the signal is shown), as illustrated in FIG. 8B. Since the sample light 48 is coherent, a single sequence of complex values 114 will contain small fluctuations that are indicative of interference (i.e., speckle interference). The processing circuitry 108 may compute a squared average of more than one sequence of complex values 114 to produce a smoother representation of the intensity of the signal light 50 as a function of optical path length 116, as illustrated in FIG. 8C.

Figure 8D:
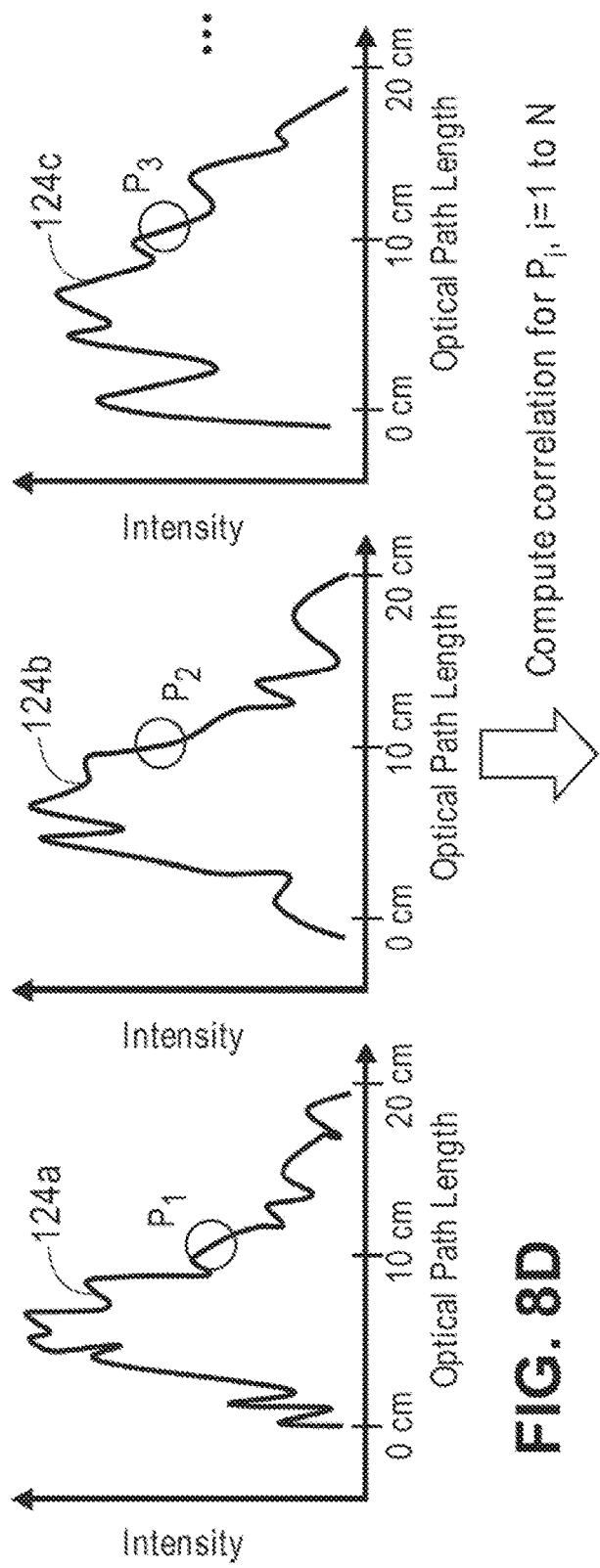
FIG. 8D are three time domain diagrams of chirped interference signals detected by the PIC used in the wearable unit of FIG. 2.
Figure 8E:
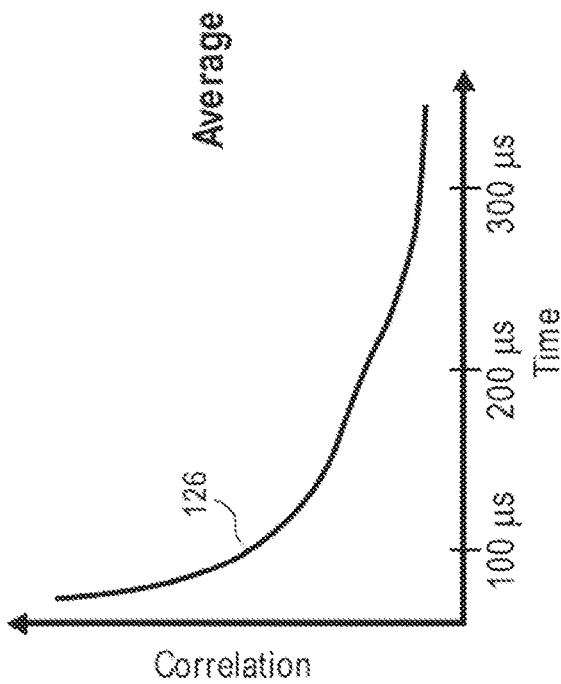
FIG. 8E is one correlation function signal detected by the PIC used in the wearable unit of FIG. 2.

The processing circuity 108 may then compute a correlation curve from the complex values 114. For example, the processing circuitry 108 may compute the Fourier transform of the values detected in three different chirp intervals as a function of time to acquire three exemplary sequences 124a, 124b, and 124c of amplitude and phase of the detected signal light 50 as a function of optical path length (here, only the magnitude of each signal is shown), as illustrated in FIG. 8D. For each sequence of amplitude and phase values as a function of optical path length, it is possible to select one value at a particular path length of interest, marked P1, P2 and P3 for curves 124a, 124b, and 124c, respectively, and then compute a temporal correlation between P1, P2 and P3 as a function of time. In practice, there will be more than three values for more than three sequences of amplitude and phase values as a function of optical path length. Denoting the number of sequences of amplitude and phase values used to compute a temporal correlation as N, the processing circuity 108 can use a value of N that ranges from 100 to 10^6. The result of computing the temporal correlation will be a correlation curve 126, as illustrated in FIG. 8E. Repeating this process multiple times will yield multiple correlation curves 126 as a function of time, and the variation in the shape of the correlation curve 126 as a function of time can be used as a measure of neural activity.

The physiological-encoded data 110 output by the processing circuitry 108 of each PIC 30 is encoded with both the occurrence and spatial depth (z-dimension) of the relevant physiological event in the brain 12, while the location of the relevant physiological event in the brain 12 is encoded in the geometric information of the spatially resolved optical paths 14. Thus, the CPU 36 may localize the physiological event in the brain 12 in three-dimensions based on the physiological-encoded data 110 output by the processing circuitry 108 (e.g., determining a spatial depth of the physiological event within the anatomical structure 12 based on the optical path length information, and determining a location of the physiological event within a two-dimensional plane along a surface of the anatomical structure 12 based on the geometric information defining locations of the PICs 30 relative to each other), as described in U.S. Provisional Patent Application Ser. No. 62/692,074, entitled "Frequency Domain Optical Spectroscopy For Neural Decoding," U.S. Patent application Ser. No. 16/379,090, entitled "Non-Invasive Frequency Domain Optical Spectroscopy For Neural Decoding," and U.S. Provisional Patent Application Ser. No. 62/722,152, entitled "Time of Flight Optical Measurement and Decoding of Fast Signals", which are expressly incorporated herein by reference.

Figure 9:
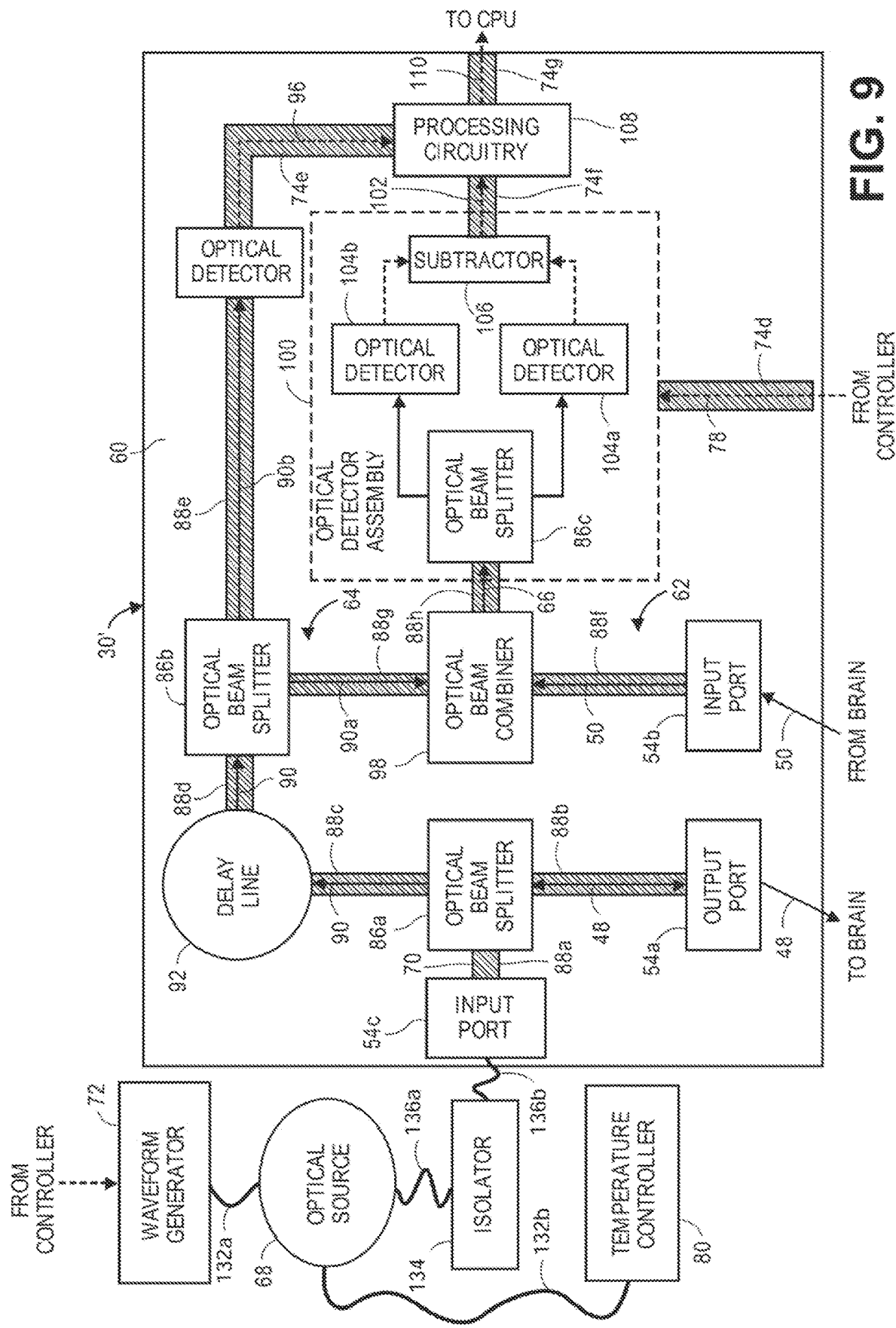
FIG. 9 is a block diagram of the detailed componentry of another embodiment of a PIC for use in the wearable unit of FIG. 2.

Referring now to FIG. 9, another embodiment of a wearable unit is similar to the previously described wearable unit 20, with the exception that the optical source 68, waveform generator 72, and temperature controller 80 are not embodied in PIC, but rather are external to a PIC 30'. This implementation would be most useful when the type of the optical source 68 cannot be composed of a material that is compatible with the material of the substrate 60 (e.g., a VCSEL), for example, if the substrate is silicon (i.e., a I-IV material), and if the optical source 68 must be composed of a III-V material that is not easily bondable or otherwise integratable with silicon.

The PIC 30' comprises an input port 54b monolithically integrated in the substrate 60. The input port 54b may take the form of a grating coupler that is disposed directly on the planar surface of substrate 60, e.g., on the opposite planar surface to the output port 54a and input port 54b. The waveform generator 72 is electrically coupled to the optical source 68 via an electrical conduit 132a, and is configured for driving the optical source 68 to vary the optical wavelength of the source light 70, and thus the sample light 48, over time. The temperature controller 80 is electrically coupled to the optical source 68 via an electrical conduit 132b, and is configured for maintaining the optical source 68 at a baseline operating temperature, such that the actual optical wavelength range of the source light 70 (and thus the sample light 48) does not vary substantially from the nominal optical wavelength range of the source light 70. The non-invasive optical measurement system 10 further comprises an optical isolator 134 optically coupled to the output of the optical source 68 via an optical fiber 136a, and is further optically coupled to the input port 54b of the PIC 30' via an optical fiber 136b. The optical isolator 134 is configured for allowing the propagation of source light 70 in one direction into the PIC 30', while preventing unwanted feedback from the PIC 30' into the optical source 68.

Although the PIC 30 (and 30') illustrated in FIGS. 6 and 9 have been described as performing interferometric-based detection of intensity and phase changes of the signal light 50 as a function of optical path length, in alternative embodiments, the PIC 30 (or 30') may implement a non-interferometric-based detection of intensity and phase changes of the signal light 50 as a function of optical path length (i.e., without a reference arm). In this case, the sample light 48 and source light 70 may be one in the same. In the case where interferometry is not used, it is preferable that a high frequency optical detector be used to directly detect the signal light 50 (without an interference light pattern), e.g., one that detects the signal light 50 at a 500 MHz to 5 GHz sampling rate. Furthermore, alternative post-processing techniques, besides a direct FFT, can be applied to the physiological-encoded electrical signal 102. For example, before computing the mean of the intensity values and phase values of the electrical signal 102, direct de-noising and feature detection may provide a means to detect and localize the relevant physiological event. Additionally, the optical wavelength sweep of the sample light 48 need not be linear, but instead could utilize any type of discrete or continuous manner to probe the brain 12 with a specific range of optical frequencies at different instances of time.

Figure 10:
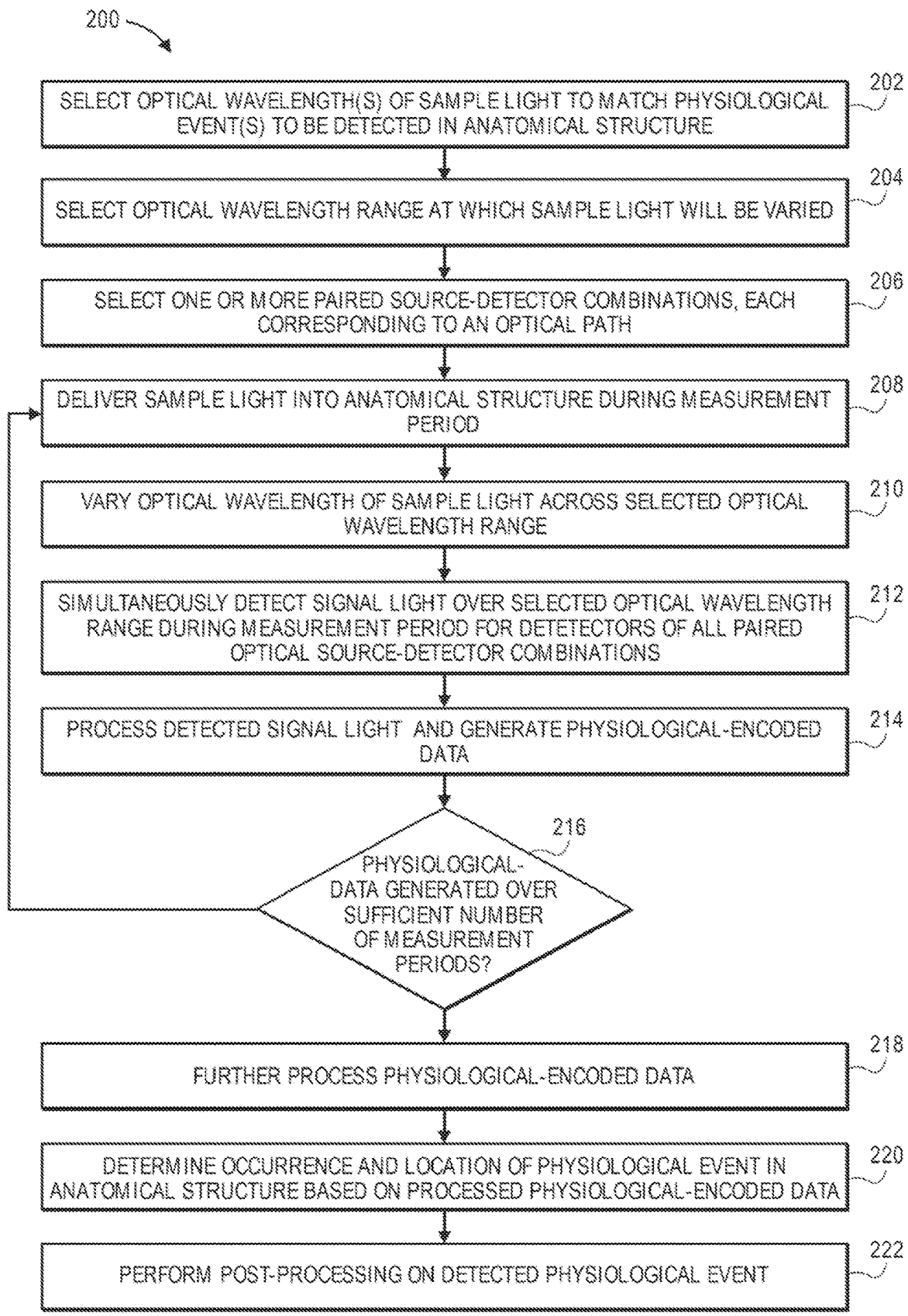
FIG. 10 is a flow diagram illustrating one method used by the optical measurement systems of FIG. 1 to non-invasively detect and localize a physiological event within an anatomical structure.

Referring to FIG. 10, having described the structure and function of the non-invasive optical measurement system 10, one particular method 200 performed by the non-invasive optical measurement system 10 to non-invasively determine the occurrence and three-dimensional location of physiological event in the brain 12 will now be described.

First, the optical wavelength(s) of the sample light 48 is selected to match the physiological event(s) to be detected in the brain 12 (step 202). In this case, the physiological event is a fast-optical signal, in which case, one optical wavelength may be greater than 850 nm. In the case where it is desirable to additionally detect blood oxygen concentration, another optical wavelength may be selected to be in the range of 650 nm to 750 nm.

Next, the optical wavelength range at which the sample light 48 will be varied is selected (e.g., 1050 nm to 1070 nm) (step 204). The paired optical source-detector combinations, each corresponding to an optical path 14, are then defined (step 206). That is, during a measurement, each PICs 30 is determined to be either an optical source, an optical detector, or both. The paired optical source-detector combination(s) may be between the same PICs 30 and/or between different PICs 30.

Next, the sample light 48 is delivered into the brain 12 by each of the PICs 30 that serve as an optical source of each paired optical source-detector combination during a single measurement period, resulting in signal light 50 that exits the brain 12 (step 208). While the sample light 48 is delivered into the brain 12, its optical wavelength is varied during the measurement period across the selected optical wavelength range (step 210). Sample light 48 may be sequentially delivered from the multiple optical sources over several measurement periods or may be delivered simultaneously from the multiple optical sources in a single measurement period. In the latter case, the sample light 48 delivered by the multiple optical sources can be distinguished if the paired optical source-detector combinations are relatively distant from each other. Even if the paired optical source-detector combinations are relatively close to each other, the sample light 48 delivered by the multiple optical sources can be distinguished via interference (i.e., sample light 48 that are delivered from other optical sources at the same time will not interfere with the sample light 48 delivered by the optical source of interest, and will instead simply add to the detected background light, which can be subtracted via the balanced detector assembly 100). Alternatively, the optical wavelengths of the sample light 40 delivered simultaneously by the multiple optical sources may different from each other at any given time to further enable optical wavelength multiplexing of the sample light 48. In any event, the optical wavelength of the sample light 48 from the optical source of each paired optical source-detector combination may be sequentially varied, e.g., by sweeping the optical wavelength of the sample light 48 over the defined optical wavelength range within the measurement period.

While the optical wavelength of the sample light 48 delivered into the brain 12 is varied over the selected optical wavelength range, the signal light 42 is simultaneously detected (i.e., sampled across the optical wavelength range) over the selected optical wavelength range by all of the PICs 30 that serve as optical detectors during the measurement period (step 212). Each of the PICs 30 that serves as an optical detector then processes the detected signal light 42 (e.g., Fourier-transforming the values detected during each measurement period, computing the mean of the intensity values and phase values over the pixels for each sample time bin, and/or computing the autocorrelation of the intensity and phase values across multiple measurement periods for one or more time bins), and generates the physiological-encoded data 110 (step 214).

If the physiological-encoded data 110 has not been generated over a sufficient number of measurement periods (step 216), steps 208-214 can be repeated. If the physiological-encoded data 110 has been acquired over a sufficient number of measurement periods (step 216), each of the PICs 30 that serve as an optical detector further processes the physiological-encoded data 100 over the measurement periods (e.g., computing the mean of the physiological-encoded data 110 over the measurement periods for each sampled frequency), and transforming the physiological-encoded data 110 from a frequency domain representation to a time domain representation to obtain intensity-optical path length information of the signal light 50 (step 218).

The CPU 36 then determines the occurrence and three-dimensional location of the relevant physiological event in the brain 12 based on the physiological-encoded data 110 (step 220). The CPU 36 may then perform post-processing on the determined physiological event, e.g., determining the level and location of neural activity within the brain 12 based on the determined location of the physiological event within the brain 12 (step 222).

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A photonic integrated circuit (PIC), comprising:
    a semiconductor substrate configured for being disposed adjacent an anatomical structure;
    an optical source monolithically integrated with the substrate; the optical source configured for generating source light;
    an optical beam splitter monolithically integrated with the substrate, the optical beam splitter optically coupled to the first optical waveguide for splitting the source light into the sample light and reference light;
    an optical delay line monolithically integrated with the substrate; the optical delay line optically coupled to the optical beam splitter for delaying the propagation of the reference light;
    an output port monolithically integrated with the substrate, the output port optically coupled to the optical source for emitting the sample light into the anatomical structure, such that the sample light is scattered by the anatomical structure, resulting in physiological-encoded signal light that exits the anatomical structure;
    an input port monolithically integrated with the substrate, the input port configured for receiving the physiological-encoded signal light from the anatomical structure;
    a second optical beam splitter monolithically integrated with the substrate, the second optical beam splitter optically coupled to the optical delay line for splitting the delayed reference light into first reference light and second reference light;
    an optical beam combiner monolithically integrated with the substrate, the optical beam combiner optically coupled to the input port and the second beam splitter for combining the physiological-encoded signal light and the first reference light into an interference light pattern;
    an optical detector monolithically integrated with the substrate, the optical detector optically coupled to the optical beam combiner for detecting the physiological-encoded signal light within the interference light pattern and generating a physiological-encoded electrical signal; and
    a normalizing optical detector monolithically integrated with the substrate, the normalizing optical detector configured for detecting the second reference light and generating a normalizing electrical signal.

2. The PIC of claim 1, wherein the physiological-encoded signal light received by the input port is created from the sample light emitted by the optical source.

3. The PIC of claim 1, wherein the physiological-encoded signal light received by the input port is created from sample light generated by an optical source of another PIC.

4. The PIC of claim 1, further comprising an optical waveguide monolithically integrated with the substrate, the optical waveguide optically coupled to the optical source for propagating the sample light within the substrate, wherein the optical source is an edge-emitting optical source configured for emitting the sample light within the optical waveguide in a direction along a plane of the substrate.

5. The PIC of claim 4, wherein the optical source comprises a distributed feedback (DFB) laser.

6. The PIC of claim 5, wherein the output port is configured for emitting the sample light into the anatomical structure in a direction perpendicular to the planar surface of the substrate, and the input port is configured for receiving the physiological-encoded signal light from the anatomical structure in a direction perpendicular to the planar surface of the substrate.

7. The PIC of claim 1, wherein each of the output port and the input port comprises a diffraction grating coupler.

8. The PIC of claim 1, further comprising a waveform generator monolithically integrated with the substrate, the waveform generator configured for outputting an electrical drive signal, wherein the optical source is electrically coupled to the waveform generator for receiving the electrical drive signal, such that the optical wavelength of the sample light is varied.

9. The PIC of claim 1, further comprising a temperature controller monolithically integrated with the substrate, the temperature controller configured for maintaining the optical source at a baseline operating temperature.

10. The PIC of claim 1, wherein the optical detector is a balanced optical detector comprising an optical beam splitter configured for splitting a third interference light pattern into first and second phase-delayed interference light patterns, first and second pixel arrays for detecting the first and second phase-delayed interference light patterns, and an arithmetic unit for subtracting the first and second phase-modulated interference light patterns to extract an alternating current (AC) component of the interference light pattern, wherein the physiological-encoded signal light is detected in the AC component of the interference light pattern.

11. The PIC of claim 1, further comprising processing circuitry monolithically integrated with the substrate, the processing circuitry electrically coupled to the optical detector and the normalizing optical detector for normalizing the physiological-encoded electrical signal based on the normalizing electrical signal.

12. The PIC of claim 11, wherein the processing circuitry is configured for processing the normalized physiological-encoded electrical signal.

13. The PIC of claim 12, wherein the normalized physiological-encoded electrical signal comprises a plurality of optical frequencies, and wherein the processing circuitry is configured for processing the normalized physiological-encoded electrical signal by transforming the electrical signal from a frequency domain representation to a time domain representation.

14. The PIC of claim 1, wherein the output port is configured for emitting the sample light into the anatomical structure from a planar surface of the substrate, and the input port is configured for receiving the physiological-encoded signal light from the anatomical structure at the planar surface of the substrate.

15. The PIC of claim 1, wherein the substrate is composed of silicon.

16. A non-invasive optical measurement system, comprising:
a two-dimensional array of photonic integrated circuits (PICs) mechanically coupled to each other, each PIC being the PIC of claim 1; and
processing circuitry configured for analyzing the detected physiological-encoded signal light from each of the PICs, and based on this analysis, determining an occurrence and a three-dimensional spatial location of a physiological event in the anatomical structure.

17. The non-invasive optical measurement system of claim 16, wherein the anatomical structure is a brain.

18. The non-invasive optical measurement system of claim 17, wherein the physiological event is indicative of neural activity.

19. The non-invasive optical measurement system of claim 18, wherein the physiological event is a fast-optical signal.

20. The non-invasive optical measurement system of claim 16, further comprising a controller configured for operating each of the PICs, such that each PIC detects the physiological-encoded signal light created by the sample light emitted by the same PIC.

21. The non-invasive optical measurement system of claim 16, further comprising a controller configured for operating each of the PICs, such that each PIC detects the physiological-encoded signal light created by the sample light emitted by at least one different PIC.

22. The non-invasive optical measurement system of claim 16, further comprising a controller configured for operating each of the PICs, such that each PIC detects the physiological-encoded signal light created by the sample light emitted from the same PIC and detects physiological-encoded signal light created by the sample light emitted from at least one different PIC.

23. The non-invasive optical measurement system of claim 16, wherein the processing circuitry is configured for deriving optical path length information from the detected physiological-encoded signal light from each of the PICs, and determining a spatial depth of the physiological event within the anatomical structure based on the optical path length information.

24. The non-invasive optical measurement system of claim 23, wherein each of the PICs is configured for varying an optical frequency of the emitted sample light, wherein the processing circuitry is configured for transforming the detected physiological-encoded signal light for each of the PICs from a frequency domain representation into a time domain representation to obtain the optical path length information of the physiological-encoded signal light.

25. The non-invasive optical measurement system of claim 24, wherein each of the PICs is configured for varying the optical frequency of the emitted sample light by sweeping the frequency of the emitted sample light.

26. The non-invasive optical measurement system of claim 16, wherein the processing circuitry is configured for determining the three-dimensional spatial location of the physiological event in the anatomical structure based on the geometric information defining locations of the PICs relative to each other.

27. The non-invasive optical measurement system of claim 16, wherein each of the PICs comprises at least a portion of the processing circuitry.

28. The non-invasive optical measurement system of claim 16, wherein each of the PICs comprises an optical waveguide, and an edge emitting optical source that emits source light within the optical waveguide in a direction along a plane of the respective PIC, wherein the sample light emitted by the respective PIC is derived from the source light.

29. The non-invasive optical measurement system of claim 28, wherein the edge emitting optical source is a distributed feedback (DFB) laser.

30. The non-invasive optical measurement system of claim 16, wherein the output port and the input port of each of the PICs are disposed on a planar surface of the respective PIC.

31. The non-invasive optical measurement system of claim 16, wherein the output port of each of the PICs is configured for emitting the respective sample light into the anatomical structure in a direction perpendicular to a planar surface of the respective PIC, and the input port of each of the PICs is configured for receiving the respective physiological-encoded signal light from the anatomical structure from a direction perpendicular to the planar surface of the respective PIC.

32. A non-invasive optical measurement method using a two-dimensional array of photonic integrated circuits (PICs) mechanically coupled to each other, each PIC of the two-dimensional array being the PIC of claim 1, the method comprising:
emitting sample light from each of the PICs into an anatomical structure, such that the sample light is scattered by the anatomical structure, resulting in physiological-encoded signal light that exits the anatomical structure;
detecting the physiological-encoded signal light by each of the pics;
analyzing the detected physiological-encoded signal light from each of the PICs; and determining an occurrence and a three-dimensional spatial location of a physiological event in the anatomical structure based on the analysis.

33. The non-invasive optical measurement method of claim 32, wherein the anatomical structure is a brain.

34. The non-invasive optical measurement method of claim 33, wherein the physiological event is indicative of neural activity.

35. The non-invasive optical measurement method of claim 34, wherein the physiological event is a fast-optical signal.

36. The non-invasive optical measurement method of claim 32, wherein each of the PICs is operated, such that each PIC detects the physiological-encoded signal light created by the sample light emitted by the same PIC.

37. The non-invasive optical measurement method of claim 32, wherein each of the PICs is operated, such that each PIC detects the physiological-encoded signal light created by the sample light emitted by at least one different PIC.

38. The non-invasive optical measurement method of claim 32, wherein each of the PICs is operated, such that each PIC detects the physiological-encoded signal light created by the sample light emitted from the same PIC and detects physiological-encoded signal light created by the sample light emitted from at least one different PIC.

39. The non-invasive optical measurement method of claim 32, further comprising deriving optical path length information from the detected physiological-encoded signal light from each of the PICs, and determining a spatial depth of the physiological event within the anatomical structure based on the optical path length information.

40. The non-invasive optical measurement method of claim 39, further comprising:
varying an optical frequency of the emitted sample light for each of the PICs;
transforming the detected physiological-encoded signal light for each of the PICs from a frequency domain representation into a time domain representation to obtain the optical path length information of the physiological-encoded signal light.

41. The non-invasive optical measurement method of claim 40, wherein the optical frequency of the emitted sample light is varied for each of the PICs by sweeping the frequency of the emitted sample light.

42. The non-invasive optical measurement method of claim 32, wherein the three-dimensional spatial location of the physiological event in the anatomical structure is determined based on the geometric information defining locations of the PICs relative to each other.

43. The non-invasive optical measurement method of claim 32, wherein the sample light is emitted from a planar surface of each of the PICs, and the physiological-encoded signal light is received at the planar surface of each of the PICs.

44. The non-invasive optical measurement method of claim 43, wherein the sample light is emitted in a direction perpendicular to the planar surface of each of the PICs, and the physiological-encoded signal light is received in a direction perpendicular to the planar surface of each of the PICs.

\* \* \* \* \*